US00RE34918E

United States Patent [19]

Nagahara et al.

[11] E Patent Number: Re. 34,918

[45] Reissued Date of Patent: Apr. 25, 1995

[54] AZAAZULENE COMPOUNDS WHICH ARE USEFUL AS ANTIALLERGIC AND ANTIINFLAMMATORY AGENTS

[75] Inventors: Michiko Nagahara, Shiga; Chikara Ieda, Kusatsu; Mitsuo Mimura, Otsu; Katsuhiro Uchida, Kyoto; Soichiro Sato, Otsu; Makoto Okumura, Moriyama, all of Japan

[73] Assignee: Kaken Pharmaceutical Co., Ltd., Tokyo, Japan

[21] Appl. No.: 225,761

[22] Filed: Apr. 5, 1994

Related U.S. Patent Documents

Reissue of:

[64] Patent No.: 5,013,736
Issued: May 7, 1991
Appl. No.: 457,125
Filed: Dec. 26, 1989

[30] Foreign Application Priority Data

Dec. 27, 1988 [JP] Japan ..... 63-334974

[51] Int. Cl.[6] ..... A61K 31/40; C07D 209/02

[52] U.S. Cl. ..... 514/255; 514/313; 514/339; 514/381; 514/382; 514/412; 544/373; 546/159; 546/272; 548/250; 548/252; 548/253; 548/254; 548/516

[58] Field of Search ..... 544/373; 546/159, 272; 548/250, 253, 254, 516, 252; 514/255, 313, 339, 382, 381, 412

[56] References Cited

FOREIGN PATENT DOCUMENTS 0013664 4/1972 Japan ..... 548/516

OTHER PUBLICATIONS

Abe, Bull. Chem. Soc. Jpn., 60, 1053 (1987).

Derwent Japanese Patent Report, vol. 8, No. 11, 3A, 1969.

*Primary Examiner*—C. Warren Ivy
*Assistant Examiner*—Zinna N. Davis
*Attorney, Agent, or Firm*—Armstrong, Westerman, Hattori, McLeland & Naughton

[57] ABSTRACT

An azaazulene derivative having the general formula (I):

(I)

wherein $R^1$ is hydrogen atom or isopropyl group; the bond C---N between C at the 2-position and N at the 1-position is single bond or double bond; when the bond C---N is single bond, $R^2$ is 5-tetrazolyl group, $R^3$ is taken together with carbon atom to form carbonyl group at the 2-position, and $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula:

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group; when the bond C---N is double bond, N at the 1-position has no substituent $R^4$, $R^2$ is cyano group, and $R^3$ is amino group (Abstract continued on next page.)

Abstract —continued or a salt thereof, azido group, a diphenyl lower alkyl amino group, a substituted phenyl amino group, a substituted piperazinyl group, a substituted homopiperazinyl group, an amino acid residue bonded by N terminal group in which C terminal group is carboxyl group or a lower alkyl ester thereof, or a lower alkyl amino group which may have an alkyl amino group that may be cyclic one, or a salt thereof, which is useful as an active ingredient of an antiallergic agent and an antiinflammatory agent and has also an inhibitory activity against histamine release, 5-lipoxygenase inhibiting activity, relaxing activity of smooth musculus trachealis and inhibitory activity against carrageenin edema, and further, is useful as medicine for prevention and treatment of bronchial asthma, allergic coryza, allergic conjunctivitis, urticaria, atopic dermatitis, other inflammatory diseases or the like.

23 Claims, No Drawings

AZAAZULENE COMPOUNDS WHICH ARE USEFUL AS ANTIALLERGIC AND ANTIINFLAMMATORY AGENTS

Matter enclosed in heavy brackets [ ] appears in the original patent but forms no part of this reissue specification; matter printed in italics indicates the additions made by reissue.

*This application is a reissue application of application Ser. No. 07/457,125 filed Dec. 26, 1989, now U.S. Pat. No. 5,013,736.*

BACKGROUND OF THE INVENTION

The present invention relates to a novel and useful azaazulene derivatives and salts thereof having antiallergic activity and antiinflammatory activity which are based on inhibitory activity against chemical mediator release, 5-lipoxygenase inhibiting activity or relaxing activity of smooth musculus trachealis, a process for preparing the same, and an antiallergic agent and an antiinflammatory agent containing the same as an active ingredient.

Hitherto, there have been commercially available and studied antiallergic agents and antiinflammatory agents having different chemical structures. The compounds of the present invention having antiallergic activity and antiinflammatory activity, however, has not yet been reported in any literature.

Patients having allergic diseases such as bronchial asthma, allergic coryza, urticaria and atopic dermatitis owing to the air pollution, the structural change of house, e.g. closed level, air-conditioning or the like, increase recently. Antiallergic agents and antiinflammatory agents which are useful for prevention and treatment of these diseases by oral administration have been desired. Steroids which are used for treatment of delayed allergy such as contact dermatitis often cause a serious side effect. Therefore, non-steroidal agents which are useful for treatment of delayed allergy have been also desired.

SUMMARY OF THE INVENTION

As a results of the continuous efforts of the present inventors to obtain compounds useful for an antiallergic agent and antiinflammatory agent, the compounds which are different from on structure and have excellent activity superior to the known compounds, it has now been found that azaazulene derivatives having the general formula (I) as shown below are such compounds.

In accordance with the present invention, there is provided an azaazulene derivative having the general formula (I):

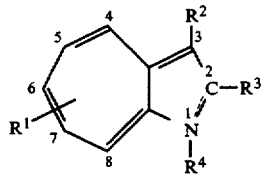

(I)

wherein $R^1$ is hydrogen atom or isopropyl group; the bond C---N between C at the 2-position and N at the 1-position is single bond or double bond; when the bond C---N single bond, $R^2$ is 5-tetrazolyl group, $R^3$ is taken together with carbon atom to form carbonyl group at the 2-position, and $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula:

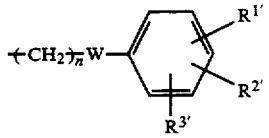

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group; when the bond C---N is double bond, N at the 1-position has no substituent $R^4$, $R^2$ is cyano group, and $R^3$ is amino group or a salt thereof, azido group, a diphenyl lower alkyl amino group, a substituted phenyl amino group, a substituted piperazinyl group, a substituted homopiperazinyl group, an amino acid residue bonded by N terminal group in which C terminal group is carboxyl group or a lower alkyl ester thereof, or a lower alkyl amino group which may have an alkyl amino group that may be cyclic one, or a salt thereof, a process for preparing an azaazulene derivative having the general formula (I'):

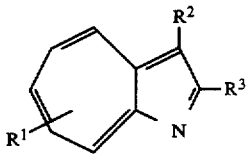

(I')

wherein $R^2$ is cyano group, $R^1$ is hydrogen atom or isopropyl group, and $R^3$ is amino group or a salt thereof, azido group, a diphenyl lower alkyl amino group, a substituted phenyl amino group, a substituted piperazinyl group, a substituted homopiperazinyl group, an amino acid residue bonded by N terminal group in which C terminal group is carboxyl group or a lower alkyl ester thereof, or a lower alkyl amino group which may have an alkyl amino group that may be cyclic one, or a salt thereof, which comprises amination of an azaazulene derivative having the general formula (II):

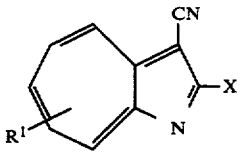

(II)

wherein $R^1$ is hydrogen atom or isopropyl group, and X is halogen atom, a process for preparing an azaazulene derivative having the general formula (I''):

(I'')

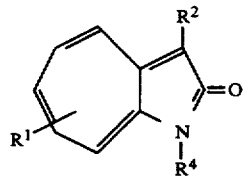

wherein $R^2$ is 5-tetrazolyl group, $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula:

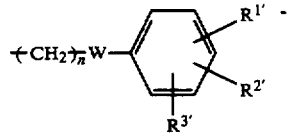

in which W is single bond or carbonyl group, oxygen atom, sulfur atom or, —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group and $R^1$ is hydrogen atom or isopropyl group, or a salt thereof, which comprises tetrazolylation of an azaazulene derivative having the general formula (III):

(III)

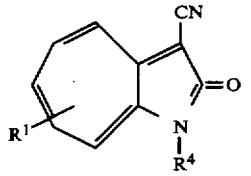

wherein $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula:

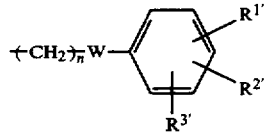

in which W is single bond or carbonyl group, oxygen atom, sulfur atom or, —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group, and $R^1$ is hydrogen atom or isopropyl group, and an antiallergic agent and antiinflammatory agent containing an azaazulene derivative having the general formula (I):

(I)

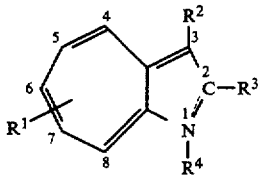

wherein $R^1$ is hydrogen atom or isopropyl group; the bond C---N between C at the 2-position and N at the 1-position is single bond or double bond; when the bond C---N is single bond, $R^2$ is 5-tetrazolyl group, $R^3$ is taken together with carbon atom to form carbonyl group at the 2-position, and $R^4$ is hydrogen atom, an alkyl group having 1 to 18 carbon atoms, a lower alkenyl group, a lower alkyl group having a oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon aromatic ring with the general formula:

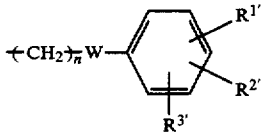

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group; when the bond C---N is double bond, N at the 1-position has no substituent $R^4$, $R^2$ is cyano group, and $R^3$ is amino group or a salt thereof, azido group, a diphenyl lower alkyl amino group, a substituted phenyl amino group, a substituted piperazinyl group, a substituted homopiperazinyl group, an amino acid residue bonded by N terminal group in which C terminal group is carboxyl group or a lower alkyl ester thereof, or a lower alkyl amino group which may have an alkyl amino group that may be cyclic one, or a salt thereof as an active ingredient.

DETAILED DESCRIPTION

Salts of the compounds having the general formula (I) of the present invention are preferably the pharmaceutically acceptable salts. When azaazulene derivatives of the present invention are represented by the general formula (I) wherein the bond C---N is double bond, $R^2$ is cyano group, $R^3$ is amino group or a salt thereof; azido group; a diphenyl lower alkyl amino group; a phenyl amino group substituted by a lower alkoxyl group, carboxyl group or a lower alkoxycarbonyl group; a piperazinyl group substituted by a diphenyl lower alkyl group or a lower alkoxyphenyl group; a homopiperazinyl group substituted by a diphenyl lower alkyl group or a lower alkoxyphenyl group; an amino acid residue bonded by N terminal group in which C terminal group is carboxyl group or a lower alkyl ester thereof; or a lower alkyl amino group which may have an alkyl amino group that may be cyclic one, and $R^1$ is hydrogen atom or isopropyl group, examples of the salts are, for instance, a salt with an inorganic acid such as hydrochloric acid, hydrobromic acid, hydroiodic acid or sulfuric acid, phosphoric acid, and a salt of an organic acid such as oxalic acid, maleic acid, tartaric acid or methanesulfonic acid, and the like. When azaazulene derivatives are represented by the general formula (I) wherein the bond C---N is single bond, $R^2$ is 5-tetrazolyl group, $R^3$ is taken together with carbon atom at the 2-position to form carbonyl group, $R^4$ is hydrogen atom, an alkyl group having 1 to 18 carbon atoms, a lower alkenyl group, a lower alkyl group having oxygen atom or sulphur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula

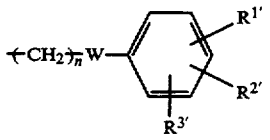

in which W is single bond or carbonyl group, oxygen atom, sulfur atom or —CH=CH—, n is an integer of 1 to 6; and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group, or cyano group, and $R^1$ is hydrogen atom or isopropyl group, examples of the salts are, for instance, salts which can be used as medicine, with a metal such as sodium, potassium, magnesium or calcium, and the like.

The compounds having the general formula (I) of the present invention and the salt thereof may be in a form of hydrate or solvate. Thus, these hydrate and solvate are also included in the compound of the present invention.

Terms used in this specification are explained below.

"Lower" substituent means a substituent having 1 to 6 carbon atoms unless otherwise specified. A lower alkenyl group, an alkyl group having 1 to 18 carbon atoms, a lower alkyl group, a lower alkoxyl group or a lower alkoxycarbonyl group may be in a form of either straight or branched.

A lower alkenyl group is a group having 2 to 6 carbon atoms and having 1 to 2 double bonds. Examples of the lower alkenyl groups are, for instance, allyl group, 2-butenyl group, and the like. Examples of the alkyl groups having 1 to 18 carbon atoms are, for instance, isopropyl group, butyl group, hexyl group, stearyl group, and the like.

Examples of the lower alkyl groups are, for instance, methyl group, ethyl group, propyl group, isopropyl group, butyl group, t-butyl group, pentyl group, and the like. Examples of the lower alkoxy groups are, for instance, methoxy group, ethoxy group, propoxy group, butoxy group, and the like.

Examples of the diphenyl lower alkyl amino groups are, for instance, diphenylmethylamino group, diphenylethylamino group, diphenylpropylamino group, and the like.

Examples of the lower alkoxycarbonyl groups are, for instance, methoxycarbonyl group, ethoxycarbonyl group, propoxycarbonyl group, t-butoxycarbonyl group, butoxycarbonyl group, and the like.

Examples of the substituted phenyl amino groups are, for instance, a phenylamino group substituted by a lower alkoxy group such as methoxyphenylamino group or ethoxyphenylamino group; a phenylamino group substituted by a lower alkoxycarbonyl group such as ethoxycarbonylphenylamino group or methoxycarbonylphenylamino group; a phenylamino group substituted by carboxyl group such as carboxyphenylamino group; and the like. Examples of the piperazinyl groups substituted at the 1-position are, for instance, a piperazinyl group substituted by a lower alkoxyphenyl group such as 2-methoxyphenylpiperazinyl group; a piperazinyl group substituted by a diphenyl lower alkyl group such as diphenylmethylpiperazinyl group; and the like. Examples of the homopiperazinyl groups substituted at the 1-position are, for instance, a homopiperazinyl group substituted by a lower alkoxyphenyl group such as 2-methoxyphenylhomopiperazinyl group; a homopiperazinyl group substituted by a diphenyl lower alkyl group such as diphenylmethylhomopiperazinyl group; and the like.

Examples of the amino acid residues bonded by N terminal group, in which C terminal group is carboxyl group or a lower alkyl ester thereof, are, for instance, glycine residue, alanine residue, phenylalanine residue, serine residue, proline residue and the like. Examples of the alkyl amino, which may be cyclic group, lower alkyl amino groups are, for instance, dimethylaminoethylamino group, pyrrolidylethylamino group and the like.

Examples of the salts of the amino groups are, for instance, a salt with an inorganic acid such as hydrochloric acid, hydrobromic acid, hydroiodic acid, sulfuric acid or phosphoric acid, and a salt with an organic acid such as oxalic acid, maleic acid, tartaric acid or methanesulfonic acid. Examples of the lower alkyl groups having oxygen atom or sulfur atom in carbon chain are, for instance, ethyloxyethyl group, ethylthioethyl group and the like. Examples of the lower alkyl groups having halogen atom or cyano group are, for instance, 3-cyanopropyl group, 3-chloropropyl group and the like.

Examples of the lower alkyl groups having heteroaromatic ring are, for instance, pyridinomethyl group, quinolylmethyl group, thienylmethyl group and the like. A halogen atom includes fluorine atom, chlorine atom, bromine atom and iodine atom. Among them, fluorine atom and chlorine atom are preferably used with excellent antiallergic activity and anti-inflammatory activity.

Examples of the suitable compounds of the present invention are the compounds represented by the general formula (I) in which the bond C---N is double bond, $R^2$ is cyano group, $R^3$ is amino group or a salt thereof; azido group; a diphenyl lower alkyl amino group; a phenyl amino group substituted by a lower alkoxyl group, carbonyl group or a lower alkoxycarbonyl group; piperazinyl group substituted by a diphenyl lower alkyl group or a lower alkoxyphenyl group; homopiperazinyl group substituted by a diphenyl lower alkyl group or a lower alkoxyphenyl group; an amino acid residue bonded by N terminal group in which C terminal group is carboxyl group or a lower alkyl ester thereof; or a lower alkyl amino group which may have an alkyl amino group that may be cyclic one, and $R^1$ is hydrogen atom or isopropyl group.

Among them, the compounds represented by the general formula (I) in which C---N is double bond, $R^2$ is cyano group, $R^3$ is azido group, diphenyl lower alkyl amino group or an amino acid residue bonded by N terminal group in which C terminal group is carboxyl group or a lower alkyl ester thereof, and $R^1$ is hydrogen atom or isopropyl group are preferable since the compounds have excellent antiallergic activity and antiinflammatory activity.

Typical examples of these compounds are, for instance, 3-cyano-2-diphenylpropylamino-1-azaazulene, 3-cyano-2-diphenylethylamino-1-azaazulene, 3-cyano-2-azido-1-azaazulene, 3-cyano-5-isopropyl-2-azido-1-azaazulene, 3-cyano-7-isopropyl-2-azido-1-azaazulene, 3-cyano-2-carboxymethylamino-1-azaazulene, 3-cyano-5-isopropyl-2-carboxymethylamino-1-azaazulene, 3-cyano-7-isopropyl-2-carboxymethylamino-1-azaazulene, 3-cyano-2-(1-carboxyethyl)amino-1-azaazulene, and the like.

Also, examples of the other suitable compounds of the present invention are the compounds represented by the general formula (I) in which the bond C---N is single bond, $R^2$ is 5-tetrazoyl group, $R^3$ is taken together with carbon atom at the 2-position to form carbonyl group, $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula:

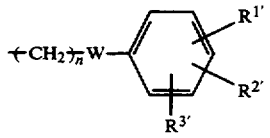

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group, and $R^1$ is hydrogen atom or isopropyl group.

Among them, the compounds represented by the general formula (I) in which the bond C---N is single bond, $R^2$ is 5-tetrazoyl group, $R^3$ is taken together with carbon atom at the 2-position to form carbonyl group, $R^4$ is hydrogen atom, a lower alkyl group having heteroaromatic ring, or a lower alkyl group having aromatic ring with the general formula:

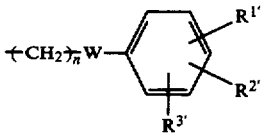

wherein W, n, $R^{1'}$, $R^{2'}$ and $R^{3'}$ are as defined above are preferable since the compounds have excellent antiallergic activity and anti-inflammatory activity.

Typical examples of these compounds are, for instance, 3-(5-tetrazoyl)-5-isopropyl-1-azaazulane-2-one, 3-(5-tetrazoyl)-7-isopropyl-1-azaasulane-2-one, 3-(5-tetrazolyl)-1-benzyl-1-azaasulane-2-one, 3-(5-tetrazolyl)-5-isopropyl-1-benzyl-1-azaazulane-2-one, 3-(5-tetrazolyl)-7-isopropyl-1-benzyl-1-azaazulane-2-one, 3-(5-tetrazolyl)-1-(4-fluorobenzyl)-1-azaazulane-2-one, 3-(5-tetrazolyl)-5-isopropyl-1-(4-fluorobenzyl)-1-azaazulane-2-one, 3-(5-tetrazolyl)-7-isopropyl-1-(4-fluorobenzyl)-1-azaazulane-2-one, 3-(5-tetrazolyl)-1-(4-chlorobenzyl)-1-azaazulane-2-one, 3-(5-tetrazolyl)-5-isopropyl-1-(4-chlorobenzyl)-1-azaazulane-2-one, 3-(5-tetrazolyl)-7-isopropyl-1-(4-chlorobenzyl)-1-azaazulane-2-one, 3-(5-tetrazolyl)-1-(3-phenylpropyl)-1-azaazulane-2-one, 3-(5-tetrazolyl)-5-isopropyl-1-(3-phenylpropyl)-1-azaazulane-2-one, 3-(5-tetrazolyl)-7-isopropyl-1-(3-phenylpropyl)-1-azaazulane-2-one, 3-(5-tetrazolyl)-1-(5-phenylpentyl)-1-azaazulane-2-one, 3-(5-tetrazolyl)-5-isopropyl-1-(5-phenylpentyl)-1-azaazulane-2-one, 3-(5-tetrazolyl)-7-isopropyl-1-(5-phenylpentyl)-1-azaazulane-2-one, 3-(5-tetrazolyl)-1-(3,4-dihydroxyphenylethyl)-1-azaazulane-2-one, 3-(5-tetrazolyl)-5-isopropyl-1-(3,4-dihydroxyphenylethyl)-1-azaazulane-2-one, 3-(5-tetrazolyl)-7-isopropyl-1-(3,--dihydroxyphenylethyl)-1-azaazulane-2-one, 3-(5-tetrazolyl)-5-isopropyl-1-(pyridino- 2-yl)methyl-1-azaazulane-2-one, 3-(5-tetrazolyl)-7-isopropyl-1-(pyridino-2-yl)methyl-1-azaazulane-2-one, and the like.

The compounds of the present invention can be prepared by the following processes.

Process (a)

Among the compounds, the compounds having the general formula (I') are easily prepared by reacting the azaazulene derivative having the general formula (II):

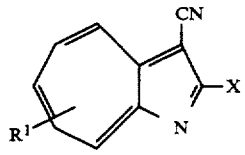

(II)

wherein $R^1$ is hydrogen atom or isopropyl group and X is halogen atom, with a amine having the general formula (IV):

$$R^5—NH_2 \quad (IV)$$

wherein $R^5$ is hydrogen atom, a diphenyl lower alkyl group, a substituted phenyl group or an alkyl amino, which may be cyclic group, lower alkyl group, or a substituted piperazine, a substituted homopiperazine, amino acid or sodium azide.

Solvents which can be used in the present reaction are not particularly limited, if the solvents do not considerably inhibit this type of reaction. In view of carrying out the reaction smoothly, examples of the suitable solvents are, for instance, an alcohol such as methanol or ethanol; a lower fatty amide such as dimethylformamide (DMF) or dimethylacetamide; and a mixture thereof. Among them, DMF, ethanol, methanol and a mixture thereof are especially preferable.

In view of carrying out the reaction smoothly, examples of the suitable bases which can be used in the present invention are, for instance, an alkali metal carbonate such as anhydrous sodium carbonate or anhydrous potassium carbonate; an alkali metal hydroxide such as sodium hydroxide or potassium hydroxide; an alkali metal hydride such as sodium hydride; an alkali metal amide such as sodium amide; and the like. Among them, anhydrous potassium carbonate, sodium hydride and sodium amide are especially preferable.

The reaction may be carried out by using an equimolecular amount of each reactant. The reaction may be, however, carried out by using an excess amount of an amines having the general formula (IV), a substituted piperazine, a substituted homopiperazine, an amino acid or sodium azide. An amines having the general formula (IV), a substituted piperazine, a substituted homopiperazine, an amino acid or sodium azide are preferably used in an amount of 1 to 1.5 moles per mole of the compound having the general formula (II).

The amount of the base may be not less than 1 mole, preferably 1.0 to 2.0 moles per mole of the compound having the general formula (II).

The reaction temperature may be optionally selected within a range from room temperature to a boiling point of the solvent, preferably, from room temperature to 100° C., and the reaction time may be optionally selected within a range from 30 minutes to 24 hours.

This process is preferably carried out by dissolving an azaazulene derivative (II) in DMF, ethanol, methanol or a mixture thereof, to the resulting solution adding an amine (IV) or a substituted piperazine, a substituted homopiperazine, an amino acid or sodium azide, optionally to the resulting mixture adding a base such as anhydrous potassium carbonate, sodium hydride or sodium amide and the mixture is stirred at a reaction temperature within a range from room temperature to 100° C. for 30 minutes to 24 hours. After the completion of the reaction, the solvent is distilled away or not, the mixture is poured into water added with ice, and the resulting precipitate is filtered. When the precipitate is not obtained, the resulting mixture is extracted with an organic solvent such as ethyl acetate or chloroform, and the solvent is distilled away to give precipitate or oily product. The precipitate or oily product is isolated and purified by usual method such as thin layer chromatography, column chromatography or recrystallization to give desired compound easily. The obtained precipitation and oily product may be subjected to the following process to obtain sodium salt of the desired compound. In 1 to 4N aqueous solution of sodium hydroxide, 1 to 4N aqueous solution of potassium hydroxide or the like is dissolved the precipitate or oily product, in case that the precipitate or oily product is not easily dissolved therein, an organic solvent such as saturated alcohol having 1 to 3 carbon atoms, acetone, acetonitrile, DMF or dimethylsulfoxide (DMSO) is added thereto, and, the mixture is reacted at room temperature to 70° C. for 20 minutes to 5 hours, and, the resulting precipitate is filtered to give sodium salt. Further, the mixture including resulting sodium salt may be neutralized or slightly acidified with an acid and be filtered to obtain an amphoteric material as a precipitate.

An azaazulene derivative (II) used as starting material in the present invention can be prepared by the method described in the literature (Daiyukikagaku, Vol. 13, P567, published by K. K. Asakurashoten, and Proc. Japan Acad., Vol. 32, P472 (1956), written by T. Nozoe, S. Seto and S. Nozoe).

Process (b)

The compounds having the general formula (I'') are easily prepared by reacting the azaazulene derivative having the general formula (III):

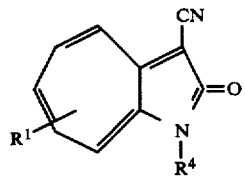

(III)

wherein $R^1$ and $R^4$ are as defined above, with hydrazoic acid or a salt thereof.

Solvents which can be used in the present reaction are not particularly limited, if the solvents do not considerably inhibit this type of reaction. In view of carrying out the reaction smoothly, examples of the suitable solvents are, for instance, hydrocarbons such as benzene, toluene and petroleum ether; aprotic polar solvents such as dimethylformamide and dimethyl sulfoxide; ethers such as dioxane, ethyl ether and tetrahydrofuran (THF); and mixtures thereof. Among them, DMF and THF are especially preferable.

Examples of the salts of hydrazoic acid used in the present reaction are, for instance, an alkali metal salt such as sodium azide, lithium azide and potassium azide; an alkaline earth metal salt such as magnesium azide, calcium azide, barium azide and strontium azide; another metal salt such as aluminium azide, tin azide, zinc azide and titanium azide; a salt with an organic acid such as ammonium azide and anilinium azide; and the like.

The salt of hydrazoic acid can be used separately, and, for instance, an alkali metal salt such as sodium azide can be used in combination with ammonium chloride or Lewis acid such as aluminium chloride, stannic chloride, zinc chloride or titanium tetrachloride.

The amounts of hydrazoic acid and salts thereof used in the present reaction, and the amount of Lewis acid or the like used in combination with the salt are about 1 to about 9 moles per mole of the azaazulene derivative (III).

The reaction temperature may be optionally selected within a range from room temperature to a boiling point of the solvent, preferably from room temperature to 120° C., and the reaction time may be optionally selected within a range from 30 minutes to 48 hours.

This process is preferably carried out by adding sodium azide or the like, and optionally aluminum chloride, ammonium chloride or the like to DMF, THF or the like, thereto then adding the above mentioned azaazulene derivative (III), and the mixture is stirred at a reaction temperature within a range from room temperature to 120° C. for 1 to 48 hours. After the completion of the reaction, the reaction mixture is poured into water added with ice, acidified with an acid, and the resulting precipitate is filtered. When the precipitate is not obtained, the resulting mixture is extracted with an organic solvent such as ethyl acetate or chloroform, and the solvent is distilled away to give precipitate. The resulting precipitate is isolated and purified by the usual method such as thin layer chromatography, column chromatography or recrystallization to give the desired compound easily.

Azaazulene derivative (III) used as starting material in the present invention can be prepared by the following method.

The azaazulene derivative (III) is easily prepared by reacting an azaazulanone derivative (V) having the general formula (V):

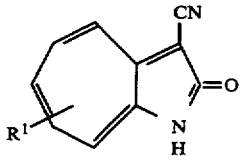

(V)

wherein $R^1$ is as defined above, with various halides having the general formula (VI):

$$X—R^4 \quad (VI)$$

wherein $R^4$ is as defined above and X is a halogen atom, in the presence of a base.

Solvents which can be used in the present reaction are not particularly limited, if the solvents do not considerably inhibit this type of reaction. In view of carrying out the reaction smoothly, examples of the suitable solvents are, for instance, hydrocarbons such as benzene and toluene; ketones such as acetone and methyl ethyl ketone; ethers such as dioxane, ethyl ether and THF; aprotic polar solvents such as DMF and DMSO; or mixtures thereof. Among them, DMF, acetone and mixture thereof are especially preferable.

In view of carrying out the reaction smoothly, examples of the suitable bases which can be used in the present reaction are, for instance, an alkali metal carbonate such as anhydrous potassium carbonate or anhydrous sodium carbonate; an alkali metal bicarbonate such as anhydrous sodium bicarbonate or anhydrous potassium bicarbonate; an alkali metal hydroxide such as sodium hydroxide or potassium hydroxide; an alkali metal hydride such as sodium hydride; and the like. Among them, anhydrous potassium carbonate and sodium hydride are especially preferable.

The reaction may be carried out by using an equimolar amount of each reactant. The reaction may be, however, carried out by using an excess amount of the various halides having the general formula (VI). The compound having the general formula (VI) are preferably used in an amount of 1.0 to 1.5 moles per mole of the compound having the general formula (V).

The amount of the base may be not less than 1 mole, preferably 1.0 to 2.0 mole per mole of the compound having the general formula (V).

The reaction temperature may be optionally selected within a range from room temperature to a boiling point of the solvent, preferably from room temperature to 80° C., and the reaction time may be optionally selected within a range from 1.0 to 48 hours.

This process is preferably carried out by dissolving the azaazulanone derivative (V) in DMF, acetone or a mixture thereof, to the resulting solution adding the halide (VI) in the presence of a base such as anhydrous potassium carbonate or sodium hydride, the mixture is stirred at a reaction temperature within a range from room temperature to 80° C. for 1 to 48 hours. After the completion of the reaction, the reaction mixture is poured into water added with ice, and the resulting precipitate is filtered. When the precipitate is not obtained, the resulting mixture is extracted with an organic solvent such as ethyl acetate or chloroform, and the solvent is distilled away to give precipitate. The precipitate is isolated and purified by the usual methods such as thin layer chromatography, column chromatography or recrystallization to give desired compound easily.

The azaazulanone derivative (V) used as starting material in this process can be prepared by the method discribed in the literature (Daiyukikagaku, Vol. 13, P567, published by K. K. Asakurashoten, and Proc. Japan Acad., Vol. 32, P472 (1956), written by T. Nozoe, S. Seto and S. Nozoe).

Depending on selection of starting material, and condition of reaction and treatment, the compounds having the general formula (I) are obtained in a form of free base or salt or hydrate. The salt can be derived by usual method, for instance, treating with a base such as sodium hydroxide.

The compounds and their salts of the present invention are pharmaceutically acceptable and useful as antiallergic agent and antiinflammatory agent, and has also an inhibitory activity against histamine release, 5-lipoxygenase inhibiting activity, relaxing activity of smooth musculus trachealis and inhibitory activity against carrageenin edema, and further, is useful as medicine for prevention and treatment of bronchial asthma, allergic coryza, allergic conjunctivitis, urticaria, atopic dermatitis, other inflammatory diseases or the like, and, for instance, in oral administration, they can be formulated in a usual manner into compositions in the form of tablet, capsule, powder and granule with conventional pharmaceutical carries. They can be also usable as injections, eye drops, nasal drops or external preparations, for example, cream, cataplasmas and inhalant.

Though the dosage of the compound of the present invention is different according to symptom, age, body weight, curative effect, route and period of administration, in oral administration, usual dosage of the compound of the present invention is preferably in the range of 10 to 3000 mg for an adult per day. The preparations can be prepared in a usual method by using any conventional carriers without any limitation in the present invention. Examples of the carriers are, for instance, binders, solid diluents, liquid diluents, fillers and the like. Typical examples of them are, for instance, starch, lactose, microcrystalline cellulose, magnesium stearate, silicic acid, talc, physiological salt solution and the like.

The azaazulene derivatives of the present invention were tested as to inhibitory activity against PCA in rat (Test Example 1-(1)), effect on carrageenin edema in a foot-pad of rat (Test Example 1-(2)), inhibitory activity against histamine release from rat mast cell (Test Example 2-(1)), relaxant activity of smooth musculus trachealis in guinea pig (Test Example 2-(2)), 5-lipoxygenase inhibiting activity in guinea pig (Test Example 2-(3)) and acute toxicity in mouse (Test Example 3). Hereinafter, No. of Examples corresponds to the compound obtained in and Examples, respectively.

TEST EXAMPLE 1

[Antiallergic activity and anti-inflammatory activity in vivo]

(1) Inhibitory activity against PCA in rat

An anti-dinitrophenylated-ovalbumin (hereinafter referred to as "anti-DNP-OVA") rat antiserum having 800 of PCA titer in homologous passive cutaneous anaphylaxis reaction in rats for 48 hours, was diluted 200 times with physiological saline, and diluted antiserum was injected intradermally into back of groups of 5 male Slc: Wistar rats weighing 130–150 g in a volume of 50 μl/site to be passively sensitized. After 48 hours, 0.6 ml of 1% (w/v) Evans blue solution containing 1.5 mg of antigen DNP-OVA was administered intravenously into the tail. Thirty minutes later, the rats were bled to death and skin of the rats was removed. According to the method of Katayama et al [Microbiol. Immunol., 22, 89 (1978)], the amount of leaked pigment of the blue dyed area was measured. The test compound was suspended in 0.5% (w/v) aqueous solution of carboxymethylcellulose (hereinafter referred to as "CMC"), the suspension was administered orally in a ratio of 5 mg/kg 1 hour before challenging an antigen.

Inhibition rate against PCA was calculated according to the following equation.

$$\text{Inhibition rate against PCA} = \frac{(M - B) - (S - B)}{(M - B)} \times 100$$

M: Amount of leaked pigment in antibody-sensitized site under administration of CMC without the test compound S: Amount of leaked pigment in antibody-sensitized site under administration of the test compound in CMC B: Amount of leaked pigment in antibody-nonsensitized site The results of the test of inhibitory activity against PCA were shown in Table 1.

TABLE 1

| Example No. | Inhibition rate against PCA (%) |
|---|---|
| 3 | 98.6 ± 3.5 |
| 4 | 78.2 ± 4.1 |
| 5 | 94.8 ± 5.1 |
| 9 | 84.9 ± 2.2 |
| 17 | −1.9 ± 9.2 |
| 30 | 10.8 ± 11.1 |
| 60 | −27.0 ± 17.7 |
| 62 | 14.0 ± 4.3 |
| repirinast*1 | 36.2 ± 5.8 |
| WP-833*2 | 42.8 ± 5.1 |

(Notes)
*1: Isopentyl 5,6-dihydro-7,8-dimethyl-4,5-dioxo-4Hpyrano[3,2-c]quinoline-2-carboxylate
*2: 5-(3-Butyloxyallylaminophenyl)-1H-tetrazole (cf. Japanese Unexamined Publication No. 11975/1982)

(2) Effect on carrageenin edema in a foot-pad of rat

The test was carried out according to the modified method on a method of Winter et al [Proc. Soc. Exp. Biol Med., 111, 544–547 (1962)]. Five male Wister rats weighing 148 to 162 g which were subjected to fasting for 24 hours were used as one group.

The test compound was suspended in 0.5% aqueous solution of CMC, and the suspension was administered orally in a amount of 50 mg/kg. After 60 minutes, 0.1 ml of 1% carrageenin solution in physiological saline was injected subcutaneously into the foot-pad of the left hind foot. Four hours after the injection of carrageenin, the volume of the foot-pad was measured by the apparatus for measurement of foot-pad volume in rat (commercially available from Ugobasile).

Swelling volume was calculated from the difference between a volume of foot-pad before inflaming the foot-pad, i.e. normal volume and that after inflaming it. Effect of a test compound was expressed as inhibition rate against swelling by calculating percentage in comparison with the 0.5% CMC administration group.

Indomethacin (commercially available from Merck Co.) was used as a positive comparative drug.

The average of the swelling volume of the 0.5% CMC administration group was 0.9 ml. The average of the swelling volume of the compound of Example No. 9 and that of Example No. 10 administration groups were 0.55 ml and 0.58 ml respectively, and the inhibition rate against swelling of the compound of Example No. 9 and that of Example No. 10 were 38.9% and 35.6% respectively. The inhibition rate against swelling of an oral administration of 5 mg/kg of Indomethacin as a positive comparative drug was 47.8%.

The results of the test of effect on carrageenin edema in a foot-pad were shown in Table 2.

TABLE 2

| Example No. | Dose mg/kg p.o. | Swelling volume 4 hours after inflaming mean ± standard error (ml) | Inhibition rate (%) |
|---|---|---|---|
| 9 | 50 | 0.55 ± 0.032 | 38.9 |
| 10 | 50 | 0.58 ± 0.036 | 35.6 |
| Control (0.5 % CMC) | — | 0.90 ± 0.035 | — |
| Indomethacin | 5 | 0.47 ± 0.056 | 47.8 |

TEST EXAMPLE2

[Antiallergic activity in vitro]

(1) Inhibitory activity against histamine release from rat mast cell

An anti-dinitrophenylated-ovalbumin (anti DNP-OVA) rat antiserum having 800 of PCA titer in homologous passive cutaneous anaphylaxis reaction in rats for 48 hours was diluted double with physiological saline, and 1 ml of diluted antiserum was injected intraperitoneally into rats to be passively sensitized. On the next day, peritoneal exudation cell (hereinafter referred to as "PEC") was collected. The collected PEC was washed with a medium containing 0.1% BSA, and $1.5 \times 10^5$ of the PEC were added to each test tube. AFter incubation at 37° C. for 10 minutes, 50 μl of test compound solution in a same medium was added thereto. After 30 seconds, 50 μl of antigen solution (DVA-OVA 100 μg/ml) was further added thereto to give the total amount of 500 μl of the reaction mixture, and histamine release reaction was induced. After 10 minutes, 1 ml of physiological saline with cooled Tris buffered solution containing 1 mM EDTA were added thereto to stop the reaction. After centrifugation, the amount of histamine in supernatant was determined by fluorescence method according to the method of Shore et al [cf. J. Pharmacol. Exp. Ther., 127, 182 (1959)]. Inhibition rate against histamine release was calculated according to the following equation.

Inhibition rate against histamine release $$\frac{(M - B) - (S - B)}{(M - B)} \times 100$$

M: Amount of histamine in supernatant under addition of antigen and non-addition of test compound S: Amount of histamine in supernatant under addition of antigen and test compound B: Amount of histamine in supernatant under non-addition of antigen and test compound.

The results of the test of inhibitory activity against histamine release were shown in Table 3. The test compound was used in a concentration of 10 μg/ml.

TABLE 3

| Example No. | Inhibitory rate (%) |
|---|---|
| 1 | 78.6 |
| 2 | 81.4 |
| 3 | 84.9 |
| 4 | 84.4 |
| 5 | 81.1 |
| 6 | 6.3 |
| 7 | 10.6 |
| 8 | 89.6 |
| 9 | 99.8 |
| 10 | 99.8 |
| 11 | 85.8 |
| 12 | 60.0 |
| 13 | 91.5 |
| 14 | 89.6 |
| 15 | 96.1 |
| 16 | 88.3 |
| 17 | 89.5 |
| 18 | 86.9 |
| 19 | 83.4 |
| 20 | 91.1 |
| 21 | 10.1 |
| 22 | 84.2 |
| 23 | 87.2 |
| 24 | 86.3 |
| 25 | 4.6 |
| 26 | 94.1 |
| 27 | 89.6 |
| 28 | 92.6 |
| 29 | 99.5 |
| 30 | 99.5 |
| 31 | 70.0 |
| 32 | 1.5 |
| 33 | 67.2 |
| 34 | 87.3 |
| 35 | 54.1 |
| 36 | 43.2 |
| 37 | 64.8 |
| 38 | 24.4 |
| 39 | 93.0 |
| 40 | 93.5 |
| 41 | 32.3 |
| 42 | 78.2 |
| 43 | 65.3 |
| 44 | 85.0 |
| 45 | 19.3 |
| 46 | 57.6 |
| 47 | 12.6 |
| 48 | 10.4 |
| 49 | 62.8 |
| 50 | 59.8 |
| 51 | 63.6 |
| 52 | 81.2 |
| 53 | 56.3 |
| 54 | 55.5 |
| 55 | 65.8 |
| 56 | 88.0 |
| 57 | 89.0 |
| 58 | 16.1 |
| 59 | 14.0 |
| 60 | 65.3 |
| 61 | 3.8 |
| 62 | 82.5 |
| 63 | 85.3 |
| 64 | −12.2 |
| 65 | 17.5 |
| 66 | 20.5 |
| 67 | 57.0 |
| 68 | 8.9 |
| 69 | 33.2 |
| 70 | 4.2 |
| 71 | 8.1 |
| 72 | 22.5 |
| 73 | 60.8 |
| 74 | 64.8 |
| 75 | −9.6 |
| 76 | 70.5 |
| 77 | 35.7 |
| 78 | 50.5 |
| 79 | 85.8 |

(2) Relaxant activity of smooth musculus trachealis in guinea pig

Male Hartley guinea pigs weighing 350 to 550 g were bleed to death, and immediately the tracheae were extirpated. According to the method of Takagi et al [cf. Chem. Pharm. Bull., 8, 716 (1958)], tracheal chain strips was prepared, and the sample was suspended on Magnus apparatus under addition of load of 0.5 g. The test was carried out at 37° C. of liquid temperature. After position of tonus was examined with histamine ($10^{-6}$ g/ml) and isoproterenol ($10^{-7}$ g/ml), the test compound dissolved in a mixture of dimethyl sulfoxide and physiological saline was added thereto, and the test compound was investigated with respect to the effect on smooth musculus trachealis. Theophylline was used as a positive comparative drug. The relaxation and the contraction of smooth musculus trachealis were recorded on servocorder (SR 6342: commercially available from Watanabe Instruments Corp.) by connecting Isotonic Transducer (TD-1125: commercially available from Nihon Kohden Kogyo Co., Ltd.) to a balancing box.

The results of the test of the relaxant activity of smooth musculas trachealis were shown in Table 4.

TABLE 4

| Example No. | Concentration for 50% relaxation (μg/ml) |
|---|---|
| 1 | 47.0 |
| 2 | 25.0 |
| 4 | 6.6 |
| 5 | 1.2 |
| 6 | 13.1 |
| 9 | 8.6 |
| 10 | 3.4 |
| 13 | 12.4 |
| 16 | 43.0 |
| 18 | 28.0 |
| 19 | 44.0 |
| 30 | 7.8 |
| 49 | 42.3 |
| 60 | 52.0 |
| theophylline | 6.8 |

(3) 5-lipoxygenase inhibiting activity in guinea pig

The test was carried out according to the method of Ochi [cf. J. Biol. Chem., 258, 5754–5758 (1983)]. Two % casein solution in saline was injected intraperitoneally into guinea pigs in an amount of 1/10 of body weight. After 16 hours, 5-lipoxygenase was prepared with polymorphonuclear leukocyte obtained from peritoneal cavity. Test compound and 5-lipoxygenase were pre-incubated at 30° C. for 10 minutes, $CaCl_2$ (calcium chloride) and $^{14}C$-arachidonic acid were added thereto, and the resulting mixture was incubated for 20 minutes. A mixture of ethyl acetate/methanol/0.2M citric acid=30/4/1 (by volume) was added thereto to stop the reaction. After centrifugation, the organic solvent layer was spotted on a plate for thin layer chromatography and developed. Effect of the test compound was determined from the amount of $^{14}C$-5-hydroxyeicosatetraenoic acid (hereinafter referred to as "5-HETE") formed from $^{14}C$-arachidonic acid. Radioactivity of 5-HETE position was measured with a liquid scintillation counter.

Inhibition rate against 5-lipoxygenase activity was calculated according to the following equation.

Inhibition rate against 5-lipoxygenase activity $$= \frac{A - B}{A} \times 100$$

A: Value of radioactivity in the control group

B: Value of radioactivity in the test compound group

The results of the test of inhibitory activity against 5-lipoxygenase activity were shown in Table 5. Each test compound was used in a concentration of 10 μM.

TABLE 5

| Example No. | Inhibition rate (%) |
|---|---|
| 3 | 63.2 |
| 4 | −1.1 |
| 5 | 1.5 |
| 6 | 27.0 |
| 7 | 60.6 |
| 9 | −5.4 |
| 10 | 41.8 |
| 13 | −9.4 |
| 29 | 17.3 |
| 30 | 12.2 |
| 35 | 34.9 |
| 38 | 31.7 |
| 43 | −7.2 |
| 44 | 18.3 |
| 46 | 41.8 |
| 48 | −1.1 |
| 49 | −2.6 |
| 51 | −2.2 |
| 62 | 5.2 |

TEST EXAMPLE 3

[Acute toxicity]

The test was carried out with the compounds obtained in Examples 5 and 9. Groups of 5 male ddy mice weighing 26 to 28 g were employed. The test compounds were suspended in a 0.5% CMC aqueous solution and the resulting suspension was administered orally in an amount of 500 for the compound obtained in Example 9, 1000 or 2000 mg/kg body weight. The survivors were kept under observation daily for 2 weeks. From the results shown in Table 6, the $LD_{50}$ of the compounds obtained in Example 5 and 9 were estimated to be more than 2000 mg/kg. The other compounds of the present invention also had the same toxicity as the above compounds.

TABLE 6

| Example No. | Dose (mg/kg P.O.) | Mortality |
|---|---|---|
| 5 | 1000 | 0/5 |
| | 2000 | 0/5 |
| 9 | 500 | 0/5 |
| | 1000 | 0/5 |
| | 2000 | 0/5 |

The present invention is more specifically described and explained by means of following Reference Examples and Examples. It is to be understood that the present invention is not limited to Examples, and various changes and modifications may be made in the invention without departing from the spirit and scope thereof. The identification of the compounds of present invention was performed by means of mass spectrum (MS), infrared absorption spectrum (IR), melting point (mp) and the like. Infrared absorption spectrum was measured according to the potassium bromide tablet method.

REFERENCE EXAMPLE 1

[3-Cyano-1-azaazulane-2-one (3-cyano-1,2-dihydrocyclohepta[b]pyrrol-2-one, 3-cyano-1,2-dihydro-1-azaazulene-2-one)]

To the mixture of 20 g (0.16 mol) of tropolone (2-hydroxy-2,4,6-cycloheptatrienone), 68 g (0.48 mol) of anhydrous potassium carbonate, 6.1 g (0.016 mol) of dicyclohexyl-18-crown-6 and 750 ml of acetonitrile were added 117 g (0.8 mol) of methyl iodide with stirring. After stirred under reflux for 10 hours, the reaction mixture was filtered. The filtrate was concentrated under reduced pressure, and the residue was dissolved in dichloromethane. After washing with 13.8% aqueous solution of potassium carbonate and water. After drying with magnesium sulfate anhydrous, dichloromethane was evaporated under reduced pressure, and the residue was subjected to purification by means of silica gel column chromatography. Elution was carried out by using ethyl acetate and the solvent was evaporated under reduced pressure to give 20 g of 2-methoxytropone (2-methoxy-2,4,6-cycloheptatrienone) (yield: 92%).

To a solution of 2.2 g (0.094 mol) of sodium metal in 300 ml of ethanol, 7.9 g (0.094 mol) of α-cyanoacetamide and solution of 13 g (0.094 mol) of 2-methoxytropone in 25 ml of ethanol was added. After stirred at room temperature for 24 to 48 hours, the reaction mixture was filtered and the filtrate was concentrated under reduced pressure. The residue was dissolved in water and resulting solution was acidified with dilute hydrochloric acid to allow precipitate. And precipitate was filtered and dried to give 12 g of title compound (yield: 75%).

Melting point: not less than 280° C.

MS m/z: 170 ($M^+$).

REFERENCE EXAMPLE 2

[3-Cyano-5-iso-propyl-1-azaazulane-2-one[3-cyano-5-(1-methylethyl)-1,2-dihydro-1-azaazulene-2-one, 3-cyano-1,2-dihydro-5-(1-methylethyl)-cyclohepta[b-]pyrrol-2-one], and 3-cyano-7-iso-propyl-1-azaazulane-2-one[3-cyano-1,2-dihydro-7-(1-methylethyl)-1-azaazulene-2-one, 3-cyano-1,2-dihydro-7-(1-methylethyl)-cyclohepta[b-]pyrrol-2-one]]

To the mixture of 100 g (0.6 mol) of hinokitiol [2-hydroxy-4-(1-methylethyl)-2,4,6-cycloheptatrienone], 165 g (1.2 mol) of anhydrous potassium carbonate, 22.5 g (0.06 mol) of dicyclohexyl-18-crown-6 and 2500 ml of acetonitrile were added 426 g (3.0 mol) of methyl iodide with stirring, and the procedure of reaction and treatment of Reference Example 1 were repeated to give 103 g mixture of 4-iso-propyl-2-methoxytropone[2-methoxy-4-(1-methylethyl)-2,4,6-cycloheptatrienone] and 6-(1-methylethyl)-2-methoxytropone[2-methoxy-6-(1-methylethyl)-2,4,6-cycloheptatrienone] (yield: 96.4%).

The procedure of Reference Example 1 were repeated except that 13.8 g (0.6 mol) of sodium metal in 2200 ml of ethanol, 50.4 g (0.6 mol) of α-cyanoacetamide and 103 g (0.58 mol) of 2-methoxy-4-iso-propyltropone were employed to give 86 g mixture of title compounds (yield: 70%). This mixture was subjected to isolation and purification by means of silica gel column chromatography. Elution was carried out by using ethyl acetate, the first fraction was collected and the solvent was evaporated under reduced pressure to give 20 g microneedles of 3-cyano-7-iso-propyl-1-azaazulane-2-one (yield: 17%).

Melting point: 186°-188° C.

MS m/z: 212 (M+).

The second fraction was collected and the solvent was evaporated under reduced pressure to give 30.5 g of 3-cyano-5-iso-propyl-1-azaazulane-2-one (yield: 25%).

Melting point 237°-239° C.

MS m/z: 212 (M+).

REFERENCE EXAMPLE 3

[3-Cyano-5-iso-propyl-1-azaazulane-2-one]

The mixture of 10 g (0.06 mol) of hinokitiol, 8 g (0.06 mol) of anhydrous potassium carbonate, 2 g (0.006 mol) of dicyclohexyl-18-crown-6, 200 ml of ethyl ether and 15 g (0.006 mol) of iodine were stirred at room temperature for 24 hours. Color of iodine disappeared and precipitate separated out. The precipitate was filtered and dissolved in water, and the solution was acidified and extracted with ethyl ether several times. The ethyl ether layer was washed with water and dried with magnesium sulfate anhydrous. Then, the ethyl ether was evaporated under reduced pressure to give 2-hydroxy-7-iodo-4-iso-propyltropone(2-hydroxy-7-iodo-4-(1-methylethyl)-2,4,6-cycloheptatrienone). The procedure of reaction and treatment of Reference Example 1 was repeated except that 17.4 g of 2-hydroxy-7-iodo-4-iso-propyltropone, 16.5 g (0.12 mol) of anhydrous potassium carbonate, 2.2 g (0.006 mol) of dicyclohexyl-18-crown-6, 250 ml of acetonitrile and 43 g (0.3 mol) of methyl iodide were employed to give 16 g of 7-iodo-2-methoxy-4-iso-propyltropone(7-iodo-2-methoxy-4-(1-methylethyl)-2,4,6-cycloheptatrienone) (yield: 90%).

MS m/z: 304 (M+), 274 ($M^+—CH_3—CH_3$), 261 ($M^+CH(CH_3)_2$).

The mixture of 13 g (0.043 mol) of 7-iodo-2-methoxyl-4-iso-propyltropone, 200 ml of methanol, 3.5 g (0.043 mol) of sodium acetate, 2 g of 5% palladium carbon was stirred at room temperature for 2 hours under hydrogen atomosphere. The reaction mixture was filtered and the filtrate was concentrated under reduced pressure to give 7.6 g of 2-methoxy-4-iso-propyltropone (yield: 100%).

MS m/z: 178 (M+), 147 ($M^+—OCH_3$), 135 ($M^+—CH(CH_3)_2$).

The procedure of reaction and treatment of Reference Example 1 were repeated except that 2 g (0.043 mol) of sodium metal, 200 ml of ethanol, 3.6 g (0.043 mol) of α-cyanoacetamide and 7.6 g (0.043 mol) of 2-methoxy-4-iso-propyltropone were employed to give 7.3 g of title compound (yield: 80%).

Spectral data (IR, MS) of the product obtained from Reference Example 3 were identical in every respect with those of the product obtained from Reference Example 2.

REFERENCE EXAMPLE 4

[2-Chloro-3-cyano-1-azaazulene(2-chloro-3-cyanocyclohepta[b]pyrrol)]

The mixture of 17 g (0.1 mol) of 3-cyano-1-azaazulane-2-one and 85 ml of phosphorous oxychloride were stirred under reflux for 1 to 1.5 hours. After cooling to room temperature, the reaction mixture was poured into water with ice and the resulting precipitate was filtered. After drying, the precipitate was extracted with chloroform and chloroform was evaporated under reduced pressure to give 14.3 g of title compound (yield: 76.1%).

Melting point: 215°-217° C.

MS m/z: 190 $M^{30}$ +2), 188 (M+), 153 (M+—Cl).

REFERENCE EXAMPLE 5

[2-Chloro-3-cyano-5-iso-propyl-1-azaazulene(2-chloro-3-cyano-5-(1-methylethyl)-cyclohepta[b]pyrrol)]

The procedure of reaction and treatment of Reference Example 4 were repeated except that 3.0 g (0.014 mol) of 3-cyano-5-iso-propyl-1-azaazulane-2-one were employed to give 2.4 g of title compound (yield: 75%).

Melting point: 128°-130° C.

REFERENCE EXAMPLE 6

[2-Chloro-3-cyano-7-iso-propyl-1-azaazulene(2-chloro-3-cyano-7-(1-methylethyl)-cyclohepta[b]pyrrol)]

The procedure of reaction and treatment of Reference Example 4 were repeated except that 3.0 g (0.014 mol) of 3-cyano-7-iso-propyl-1-azaazulane-2-one were employed to give 2.5 g of title compound (yield: 78%).

Melting point: 149°-151° C.

REFERENCE EXAMPLE 7

3-Cyano-1-methyl-1-azaazulane-2-one[3-cyano-1,2-dihydro- 1-methyl-1-azaazulene-2-one, 3-cyano-1,2-dihydro-1-methyl-cyclohepta[b]pyrrol-2-one]]

To the mixture of 5 g (0.03 mol) of 3-cyano-1-azaazulane-2-one and 50 ml of dimethylformamide (DMF), 2.2 g (0.045 mol) of sodium hydride was added portion wise. After stirring at room temperature for 10 minutes, 6.4 g (0.045 mol) of methyl iodide was added stirred at room temperature for 2 to 2.5 hours. The reaction mixture was poured into water with ice, and the resulting precipitate was filtered, washed on the filter with water and dried to give 4.0 g of title compound (yield: 73%).

Melting point: 213°-233° C. (dec.).

MS m/z: 184 (M+).

REFERENCE EXAMPLE 8

[3-Cyano-1-(4-fluorophenylmethyl)-5-iso-propyl-1-azaazulane-2-one[3-cyano-1-(4-fluorophenylmethyl)-1,2-dihydro-1-azaazulene-2-one, 3-cyano-1-(4-fluorophenylmethyl)-1,2-dihydro-cyclohepta[b]pyrrol-2one]]

To the mixture of 6 g (0.03 mol) of 3-cyano-5-iso-propyl-1-azaazulane-2-one and 60 ml of DMF, 4.2 g (0.03 mol) of anhydrous potassium carbonate was added. After stirring at room temperature for 10 minutes, 5.7 g (0.03 mol) of 4-fluorobenzyl bromide was added, and resulting mixture was stirred at room temperature for 3 hours. The reaction mixture was poured into water with ice, and the resulting precipitate was filtered and washed on the filter with water. After drying, the precipitate was washed with petroleum ether to give 9.6 g of title compound (yield: 100%).

Melting point: 145°-147° C. (dec.).

MS m/z: 320 (M+), 277 ($M^+—CH(CH_3)_2$).

REFERENCE EXAMPLES 9 to 58

The procedures of reaction and treatment of Reference Example 7 or 8 were repeated except that corresponding starting compounds were employed instead of 3-cyano-1-azaazulane-2-one or 3-cyano-5-iso-propyl-1-azaazulane-2-one to give compounds represented by the general formul (III):
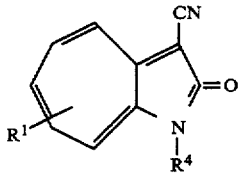
(III)
wherein $R^1$ and $R^4$ were as shown in Table 7. Melting point and mass spectrum of obtained compounds are shown in Table 7.

TABLE 7

| Ref. Ex. No. | $R^1$ | $R^4$ | Melting point (°C.) | MS(m/z) |
|---|---|---|---|---|
| 9 | 7-$CH(CH_3)_2$ | $CH_3$ | 199-201 | 226($M^+$), 211($M^+-CH_3$) |
| 10 | H | $CH(CH_3)_2$ | 180-182 | 212($M^+$), 170($M^+-CH(CH_3)_2$) |
| 11 | H | $(CH_2)_3CH_3$ | 130-132 | 226($M^+$), 209($M^+-OH$), 184($M^+-CH_2 \times 3$), 170($M^+-CH_2 \times 4$) |
| 12 | 5-$CH(CH_3)_2$ | $(CH_2)_3CH_3$ | 89-91 | 268($M^+$), 251($M^+-OH$), 225($M^+-CH(CH_3)_2$), 212($M^+-(CH_2)_3CH_3$) |
| 13 | 7-$CH(CH_3)_2$ | $(CH_2)_3CH_3$ | 118-120 | 268($M^+$), 225($M^+-CH(CH_3)_2$), 212($M^+-(CH_2)_3CH_3$) |
| 14 | H | $(CH_2)_5CH_3$ | 95-97 | 254($M^+$), 237($M^+-OH$), 211($M^+-CH_2 \times 3$), 184($M^+-CH_2 \times 5$), 170($M^+-CH_2 \times 6$) |
| 15 | H | $(CH_2)_{17}CH_3$ | 63-65 | 422($M^+$), 405($M^+-OH$), 170($M^+-(CH_2)_{18}$) |
| 16 | H | $CH_2CH{=}CH_2$ | 146-148 | 210($M^+$), 170($M^+-CH_2CH{=}CH_2$) |
| 17 | H | $CH_2CH_2OCH_2CH_3$ | 103-105 | 242($M^+$), 213($M^+-CH_2CH_3$), 197($M^+-OCH_2CH_3$), 170($M^+-CH_2CH_2OCH_2CH_3$) |
| 18 | H | $CH_2CH_2CH_2CN$ | 149-151 | 237($M^+$), 197($M^+-CH_2CN$), 184($M^+-CH_2CH_2CN$), 170($M^+-(CH_2)_3CN$) |
| 19 | H | $CH_2CH_2CH(C_6H_5)_2$ | 157-159 | 364($M^+$), 184($M^+-CH_2CH(C_6H_5)_2$) |
| 20 | H | $CH_2C_6H_5$ | 182-184 | 260($M^+$) |
| 21 | 5-$CH(CH_3)_2$ | $CH_2C_6H_5$ | 128-130 | 302($M^+$), 259($M^+-CH(CH_3)_2$) |
| 22 | 7-$CH(CH_3)_2$ | $CH_2C_6H_5$ | 142-144 | 302($M^+$), 259($M^+-CH(CH_3)_2$) |
| 23 | H | $(CH_2)_2C_6H_5$ | 180-181 | 274($M^+$), 184($M^+-CH_2C_6H_5$) |
| 24 | 7-$CH(CH_3)_2$ | $(CH_2)_2C_6H_5$ | 199-201 | 316($M^+$), 225($M^+-CH_2C_6H_5$), 212($M^+-CH_2CH_2C_6H_5$) |
| 25 | H | $(CH_2)_3C_6H_5$ | 131-133 | 288($M^+$), 184($M^+-CH_2CH_2C_6H_5$) |
| 26 | 5-$CH(CH_3)_2$ | $(CH_2)_3C_6H_5$ | 164-166 | 330($M^+$), 287($M^+-CH(CH_3)_2$), 226($M^+-(CH_2)_2C_6H_5$), 211($M^+-(CH_2)_3C_6H_5$) |
| 27 | 7-$CH(CH_3)_2$ | $(CH_2)_3C_6H_5$ | 167-169 | 330($M^+$), 287($M^+-CH(CH_3)_2$), 226($M^+-(CH_2)_2C_6H_5$), 211($M^+-(CH_2)_3C_6H_5$ |
| 28 | H | $(CH_2)_4C_6H_5$ | 109-111 | 302($M^+$), 285($M^+-OH$), 212($M^+-CHC_6H_5$), 197($M^+-(CH_2)_2C_6H_5$), 170($M^+-(CH_2)_4C_6H_5$) |
| 29 | 7-$CH(CH_3)_2$ | $(CH_2)_4C_6H_5$ | 108-110 | 344($M^+$), 327($M^+-OH$), 301($M^+-CH(CH_3)_2$), 253($M^+-CH_2C_6H_5$), 240($M^+-(CH_2)_2C_6H_5$) |
| 30 | H | $(CH_2)_5C_6H_5$ | 118-120 | 316($M^+$), 299($M^+-OH$), 212($M^+-CH_2CH_2C_6H_5$), 170($M^+-(CH_2)_5C_6H_5$) |
| 31 | 5-$CH(CH_3)_2$ | $(CH_2)_5C_6H_5$ | 96-97.5 | 358($M^+$), 341($M^+-OH$), 267($M^+-CH_2C_6H_5$), 253($M^+-(CH_2)_2C_6H_5$), 212($M^+-(CH_2)_5C_6H_5$) |
| 32 | 7-$CH(CH_3)_2$ | $(CH_2)_5C_6H_5$ | 79-81 | 358($M^+$), 341($M^+-OH$), 267($M^+-CH_2C_6H_5$), 253($M^+-(CH_2)_2C_6H_5$), 212($M^+-(CH_2)_5C_6H_5$) |
| 33 | H | $CH_2C_6H_4F$(p) | 190-192 | 278($M^+$) |
| 34 | H | $CH_2C_6H_4F$(m) | 180-182 | 278($M^+$), 261($M^+-OH$) |
| 35 | H | $CH_2C_6H_4F$(o) | 199-201 | 278($M^+$) |
| 36 | 7-$CH(CH_3)_2$ | $CH_2C_6H_4F$(p) | 152-154 | 320($M^+$), 277($M^+-CH(CH_3)_2$) |
| 37 | H | $CH_2C_6H_4Cl$(p) | 168-170 | 296($M^+ + 2$), 294($M^+$) |
| 38 | 5-$CH(CH_3)_2$ | $CH_2C_6H_4Cl$(p) | 133-135 | 339($M^+ + 2$), 337($M^+$) |
| 39 | 7-$CH(CH_3)_2$ | $CH_2C_6H_4Cl$(p) | 145-147 | 339($M^+ + 2$), 337($M^+$) |
| 40 | H | $CH_2C_6H_4CF_3$(p) | 182-184 | 328($M^+$) |
| 41 | H | $CH_2C_6H_4CN$(p) | 188-190 | 285($M^+$) |
| 42 | H | $CH_2C_6H_4COOC_2H_5$(p) | 164-166 | 332($M^+$), 258($M^+-COOC_2H_5$) |
| 43 | H | $CH_2C_6H_4OCH_3$(p) | 174-176 | 290($M^+$), 183($M^+-C_6H_4OCH_3$(p)) |
| 44 | H | $CH_2COC_6H_4Cl$(p) | 287-289 | 324($M^+ + 2$), 322($M^+$), 183($M^+-COC_6H_4Cl$(p)) |
| 45 | H | $CH_2CH{=}CHC_6H_5$ | 178-180 | 286($M^+$), 169($M^+-CH_2CH{=}CHC_6H_5$) |
| 46 | H | $CH_2CH_2OC_6H_5$ | 184-186 | 290($M^+$), 197($M^+-OC_6H_5$) |
| 47 | H | $CH_2SC_6H_5$ | 152-154 | 292($M^+$) |

TABLE 7-continued
| Ref. Ex. No. | $R^1$ | $R^4$ | Melting point (°C.) | MS(m/z) |
|---|---|---|---|---|
| 48 | H | 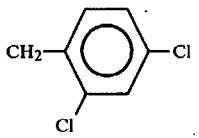 | 185–187 | 330($M^+$ + 2), 328($M^+$), 293($M^+$—Cl) |
| 49 | H | 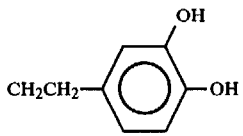 | 251–253 | 306($M^+$), 184($M^+$—$CH_2$— 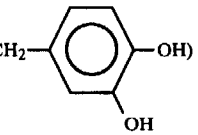 —OH) |
| 50 | H | 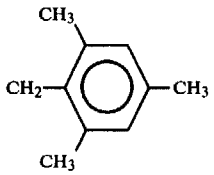 | 263–265 | 302($M^+$), 285($M^+$—OH) |
| 51 | H | 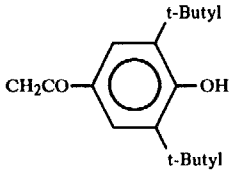 | 269–271 | 416($M^+$), 401($M^+$—$CH_3$), 233($M^+$—CO— 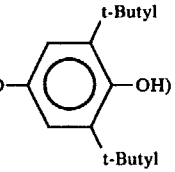 —OH) |
| 52 | H | 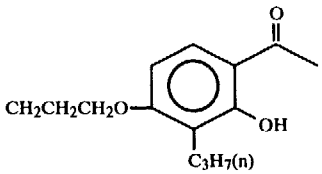 | 111–114 | 404($M^+$), 362($M^+$—$COCH_2$), 211($M^+$—O— 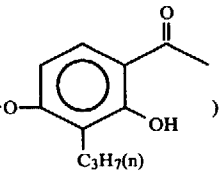 ) |
| 53 | 5-$CH(CH_3)_2$ | 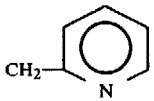 | 153–155 | 303($M^+$), 288($M^+$—$CH_3$), 260($M^+$—$CH(CH_3)_2$) |

TABLE 7-continued
| Ref. Ex. No. | $R^1$ | $R^4$ | Melting point (°C.) | MS(m/z) |
|---|---|---|---|---|
| 54 | 5-$CH(CH_3)_2$ | 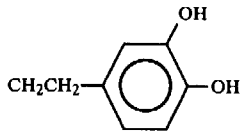 | 249-251 | 348($M^+$), 212($M^+$—$CH_2CH_2$— 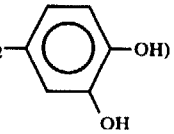 ) |
| 55 | 5-$CH(CH_3)_2$ | 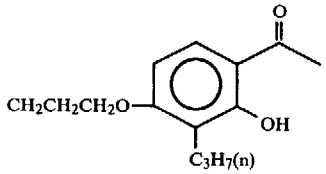 | 94-96 | 446($M^+$), 253($M^+$—O— 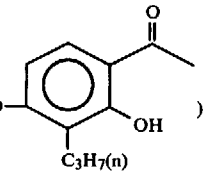 ) |
| 56 | 5-$CH(CH_3)_2$ | 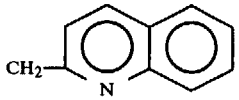 | 187-189 | 353($M^+$), 338($M^+$—$CH_3$), 310($M^+$—$CH(CH_3)_2$) |
| 57 | H | $CH_2CH_2CH_2Cl$ | 157-159 | 246($M^+$), 211($M^+$—Cl), 210($M^+$—HCl), 184($M^+$—$(CH_2)_2Cl$), 170($M^+$—$(CH_2)_3Cl$) |
| 58 | 5-$CH(CH_3)_2$ | 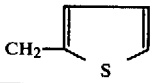 | 109-111 | 308($M^+$), 212($M^+$—$CH_2$— 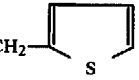 ) |

de

EXAMPLE 1

[5-Iso-propyl-3-(5-tetrazolyl)-1-azaazulane-2-one[1,2-dihydro-5(1-methylethyl)-3-(1H-tetrazol-5-yl)-1-azaazulene-2-one, 1,2-dihydro-5-(1-methylethyl)-3-(1H-tetrazol-5-yl)cyclohepta[b]pyrrol-2-one]]

To 50 ml of ice cooled absolute tetrahydrofuran (abs. THF), 5.2 g (0.039 mol) of anhydrous aluminium chloride and 7.6 g (0.117 mol) of sodium azide were added. After stirring for 10 minutes, 2.8 g (0.013 mol) of 3-cyano-5-iso-propyl-1-azaazulane-2-one was added thereto, and reaction mixture was stirred for 2 hours at room temperature, and under reflux for further 1 hour. The reaction mixture was poured into water with ice, and the mixture was acidified with dilute hydrochloric acid to allow precipitation. The precipitate was washed on filter with water and dried to give 3.0 g of title compound (yield: 90%).

Melting point: 284°–286° C. (dec.).

MS m/z: 255 ($M^+$), 212 ($M^+$—$N_3H$), 199 ($M^+$—$N_2$—$N_2$), 171 ($M^+$—$N_3H$—$CH(CH_3)_2$).

IR ($cm^{-1}$): 3120–2850 (CH), 1665–1650 (CONH).

EXAMPLE 2

[7-Iso-propyl-3-(5-tetrazolyl)-1-azaazulane-2-one[1,2-dihydro-7-(1-methylethyl)-3-(1H-tetrazol-5-yl)-1-azaazulene-2-one, 1,2-dihydro-7-(1-methylethyl)-3-(1H-tetrazol-5-yl)cyclohepta[b]pyrrol-2-one]]

The procedure of reaction, treatment and purification of Example 1 were repeated except that 2.8 g (0.013 mol) of 3-cyano-7-iso-propyl-1-azaazulane-2-one was employed instead of 3-cyano-5-iso-propyl-1-azaazulane-2-one employed in Example 1 to give 3.0 g of title compound (yield: 90%).

Melting point: not less than 290° C.

MS m/z: 255 ($M^+$), 212 ($M^+$—$N_3H$), 199 ($M^+$—$N_2$-N2), 171 ($M^+$—$N_3H$—$CH(CH_3)_2$).

IR ($cm^{-1}$): 3150–2850 (CH), 1670–1650 (CONH).

EXAMPLE 3

[1-Benzyl-3-(5-tetrazolyl)-1-azaazulane-2-one[1,2-dihydro-1-phenylmethyl-3-(1H-tetrazol-5-yl)-1-azaazulene-one, 1,2-dihydro-1-phenylmethyl-3-(1H-tetrazol-5-yl)cyclohepta[b]pyrrol-2-one]]

The procedure of reaction, treatment and purification of Example 1 were repeated except that 2.6 g (0.01 mol) of 3-cyano-1-benzyl-1-azaazulane-2-one[3-cyano-1,2-dihydro-1-phenylmethyl-1-azaazulene-2-one, 3-cyano-1,2-dihydro-1-phenylmethyl-cyclohepta[b]pyrrol-2one] was employed instead of 3-cyano-5-iso-propyl-1-azaazulane-2-one and reacted at room temperature for 1.5 hours to give 2.7 g of title compound (yield: 89%).

Melting point: 273°–275° C. (dec.).

MS m/z: 303 ($M^+$—$N_3H$), 247 ($M^+$—$N_2$—$N_2$).

IR ($cm^{-1}$): 3150–2850 (CH), 1660–1650 (CON).

EXAMPLE 4

[5-Iso-propyl-1-benzyl-3-(5-tetrazolyl)-1-azaazulane-2-one[1,2-dihydro-5-(1-methylethyl)-1-phenylmethyl-3-[1H- tetrazol-5-yl)-1-azaazulene-2-one, 1,2-dihydro-5-(1-methylethyl)-1-phenylmethyl-3-(1 H-tetrazol-5-yl)cyclohepta[b]pyrrol-2-one]]

The procedure of reaction, treatment and purification of Example 1 were repeated except that 3.0 g (0.01 mol) of 3-cyano-5-iso-propyl-1-benzyl-1-azaazulane-one[3-cyano-1,2-dihydro-5-(1-methylethyl)-1-phenylmethyl-1-azaazulene-2-one, 3-cyano-1,2-dihydro-5-(1-methylethyl)-1-phenylmethyl-cyclohepta[b]pyrrol-2-one] was employed instead of 3-cyano-5-iso-propyl-1-azaazulane-2-one and reacted at room temperature for 3.5 hours to give 2.8 g of title compound (yield: 81.8%).

Melting point: 224°–226° C. (dec.).

MS m/z: 345 ($M^+$), 317 ($M^+$—$N_2$), 302 ($M^+$—$N_3H$), 289 ($M^+$—$N_2$—$N_2$).

IR ($cm^{-1}$), 3190–2850 (CH), 1660–1650 (CON).

EXAMPLE 5

[7-Iso-propyl-1-benzyl-3-(5-tetrazolyl)-1-azaazulane-2-one[1,2-dihydro-7-(1-methylethyl)-1-phenylmethyl-3-(1H-tetrazol-5-yl)-1-azaazulene-2-one, 1,2-dihydro-7-(1-methylethyl)-1-phenylmethyl-3-(1 H-tetrazol-5-yl)cyclohepta[b]pyrrol-2-one]]

The procedure of reaction, treatment and purification of Example 1 were repeated except that 3.0 g (0.01 mol) of 3-cyano-7-iso-propyl-1-benzyl-1-azaazulane-2-one[3-cyano-1,2-dihydro-7-(1-methylethyl)-1-phenylmethyl-1-azaazulene-2-one, 3-cyano-1,2-dihydro-7-(1-methylethyl)-1-phenylmethyl-cyclohepta[b]pyrrol-2-one] was employed instead of 3-cyano-5-iso-propyl-1-azaazulane-2-one and reacted at room temperature for 3.5 hours to give 3.5 g of title compound (yield: 99.7%).

Melting point 268°–270° C. (dec.).

MS m/z: 345 ($M^+$), 317 ($M^+$—$N_2$), 302 ($M^+$—$N_3H$), 289 ($M^+$—$N_2$—$N_2$).

IR ($cm^{-1}$): 3180–2850 (CH), 1680–1670 (CON).

EXAMPLE 6

[5-Iso-propyl-1-(5-phenylpentyl)-3-(5-tetrazolyl)-1-azaazulane-2-one[1,2-dihydro-5-(1-methylethyl)-1-(5-phenylpentyl)-3-(1H-tetrazol-5-yl)-1-azaazulene-2-one, 1,2-dihydro-5-(1-methylethyl)-1-(5-phenylpentyl)-3-(1 H-tetrazol-5-yl)-cyclohepta[b]pyrrol-2-one]]

The procedure of reaction, treatment and purification of Example 1 were repeated except that 3.6 g (0.01 mol) of 3-cyano-5-iso-propyl-1-(5-phenylpentyl)-1-azaazulane-2-one [3-cyano-1,2-dihydro-5-(1-methylethyl)-1-(5-phenylpentyl)-1-azaazulene-2-one, 3-cyano-1,2-dihydro-5-(1-methylethyl)-1-(5-phenylpentyl)cyclohepta[b-]pyrrol-2-one] was employed instead of 3-cyano-5-iso-propyl-1-azaazulane-2-one and reacted at room temperature for 3 hours to give 3.9 g of title compound (yield: 95.6%).

Melting point: 143°–145° C. (dec.).

MS m/z: 401 ($M^+$), 373 ($M^+$—$N_2$), 358 ($M^+$—$N_3H$), 345 ($M^+$—$N_2$—$N_2$), 328 ($M^+$—$N_3H$—$CH_3X2$).

IR ($cm^{-1}$): 3160–2850 (CH), 1660 (CON).

EXAMPLE 7

[7-Iso-propyl-1-(5-phenylpentyl)-3-(5-tetrazolyl)-1-azaazulane-2-one[1,2-dihydro-7-(1-methylethyl)-1-(5-phenylpentyl)-3-(1 H-tetrazol-5-yl)-1-azaazulene-2-one, 1,2-dihydro-7-(1-methylethyl)-1-(5-phenylpentyl)-3-(1 H-tetrazol-5-yl)-cyclohepta[b]pyrrol-2-one]]

The procedure of reaction, treatment and purification of Example 1 were repeated except that 3.6 g (0.01 mol) of 3-cyano-7-iso-propyl-1-(5-phenylpentyl)-1-azaazulane-2-one[3-cyano-1,2-dihydro-7-(1-methylethyl)-1-(5-phenylpentyl)-1-azaazulene-2-one, 3-cyano-1,2-dihydro-7-(1-methylethyl)-1-(5-phenylpentyl)-cyclohepta[b-]pyrrol-2-one] was employed instead of 3-cyano-5-isopropyl-1-azaazulane- 2-one and reacted at room temperature for 3 hours to give 3.7 g of title compound (yield: 91.9%).

Melting point: 184°-186° C. (dec.).

MS m/z: 401 ($M^+$), 373 ($M^+$—$N_2$), 358 ($M^+$—$N_3H$), 345 ($M^+$—$N_2$—$N_2$), 328 ($M^+$—$N_3H$—$CH_3X2$).

IR ($cm^{-1}$): 3130–2850 (CH), 1680–1670 (CON).

EXAMPLE 8

[1-(4-Fluorobenzyl)-3-(5-tetrazolyl)-1-azaazulane-2-one]

The procedures of reaction, treatment and purification of Example 1 were repeated except that 2.8 g (0.01 mol) of 3-cyano-1-(4-fluorobenzyl)-1-azaazulane-2-one was employed instead of 3-cyano-5-isopropyl-1-azaazulane-2-one and reacted at room temperature for 2 hours to give title compound (yield: 95%).

Melting point: 282°-284° C. (dec.).

MS m/z:321 ($M^+$), 278 ($M^+$—$N_3H$), 265 ($M^+$—$N_2$—$N_2$).

IR ($cm^{-1}$): 3200–2850 (CH), 1670–1660 (CON).

EXAMPLE 9

[1-(4-Fluorobenzyl)-5-iso-propyl-3-(5-tetrazolyl)-1-azaazulane-2-one]

The procedures of reaction, treatment and purification of Example 1 were repeated except that 3.2 g (0.01 mol) of 3-cyano-1-(4-fluorobenzyl)-5-iso-propyl-1-azaazulane-2-one was employed instead of 3-cyano-5-iso-propyl-1-azaazulane-2-one and reacted at room temperature for 2.5 hours to give title compound (yield: 90.9%).

Melting point: 266°-268° C. (dec.).

MS m/z: 363 ($M^+$), 335 ($M^+$—$N_2$), 320 ($M^{30}$—$N_3H$), 307 ($M^+$—N—$_2$—$N_2$).

IR ($cm^{-1}$): 3120–2850 (CH), 1660–1645 (CON).

EXAMPLE 10

[1-(4-Fluorobenzyl)-7-iso-propyl-3-(5-tetrazolyl)-1-azaazulane-2-one]

The procedures of reaction, treatment and purification of Example 1 were repeated except that 3.2 g (0.01 mol) of 3-cyano-1-(4-fluorobenzyl)-7-iso-propyl-1-azaazulane-2-one was employed instead of 3-cyano-5-iso-propyl-1-azaazulane-2-one and reacted at room temperature for 2.5 hours to give title compound (yield: 89.4%).

Melting point: 283°-285° C. (dec.).

MS m/z: 363 ($M^+$), 335 ($M^{30}$—$N_2$), 320 ($M^{30}$—$N_3H$), 307 ($M^{30}$—$N_2$—$N_2$).

IR ($cm^{-1}$): 3160–2850 (CH), 1670–1660 (CON).

EXAMPLE 11

[1-(4-Chlorobenzyl)-3-(5-tetrazolyl)-1-azaazulane-2-one]

The procedures of reaction, treatment and purification of Example 1 were repeated except that 2.9 g (0.01 mol) of 1-(4-chlorobenzyl)-3-cyano-1-azaazulane-2-one was employed instead of 3-cyane-5-iso-propyl-1-azaazulane-2-one and reacted at room temperature for 2 hours to give title compound (yield: 95.7%).

Melting point: 255°-257° C. (dec.).

MS m/z: 339 ($M^+$ +2), 337 ($M^+$), 294 ($M^+$—$N_3H$), 281 ($M^+$—$N_2$—$N_2$).

IR ($cm^{-1}$): 3160–2850 (CH), 1650–1640 (CON).

EXAMPLE 12

[1-(3,4-Dihydroxyphenylethyl)-5-iso-propyl-3-(5-tetrazolyl)-1-azaazulane-2-one]

The procedures of reaction, treatment and purification of Example 1 were repeated except that 3.5 g (0.01 mol) of 1-(3,4-dihydroxyphenylethyl)-3-cyano-5-iso-propyl-1-azaazulane-2-one was employed instead of 3-cyano-5-iso-propyl-1-azaazulane-2-one and reacted at room temperature for 2.5 to 3 hours to give title compound (yield: 90.6%).

Melting point: 265°-267° C. (dec.).

MS m/z: 391 ($M^+$), 363 ($M^+$—$N_2$), 348 ($M^+$—$N_3H$), 335 ($M^+$—$N_2$—$N_2$), 323 ($M^+$—$CN_4$).

IR ($cm^{-1}$): 3150–2850 (CH), 1650 (CON).

EXAMPLE 13

[5-Iso-propyl-1-(2-pyridylmethyl)-3-(5-tetrazolyl)-1-azaazulane-2-one]

The procedures of reaction, treatment and purification of Example 1 were repeated except that 3.0 g (0.01 mol) of 3-cyano-5-iso-propyl-1-(2-pyridylmethyl)-1-azaazulane-2-one was employed instead of 3-cyano-5-iso-propyl-1-azaazulane-2-one and reacted at room temperature for 2.5 hours to give title compound (yield: 96.8%).

Melting point: 289°-291° C. (dec.).

MS m/z: 346 ($M^+$), 318 ($M^+$—$N_2$), 303 ($M^+$—$N_3H$), 290 ($M^+$—N—$N_2$), 275 ($M^+$—$N_2$—$N_2$—$CH_3$).

IR ($cm^{-1}$): 3160–2850 (CH), 1660–1650 (CON).

EXAMPLES 14 TO 57

The procedures of reaction, treatment and purification of Example 1 were repeated except that corresponding starting compounds were employed instead of 3-cyano-5-isopropyl-1-azaazulane-2-one to give compounds represented by the general formula (I''):

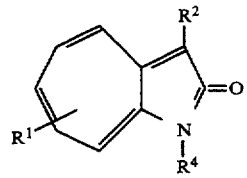

(I'')

wherein $R^1$ and $R^4$ were as shown in Table 8, and $R^2$ was tetrazolyl group.

Yield and Melting point of obtained compounds are shown in Table 8 in which "dec." means decomposition, and MS and IR of obtained compounds are shown in Table 9.

TABLE 8

| Ex. No. | $R^1$ | $R^4$ | Yield (%) | Melting point (°C.) |
|---|---|---|---|---|
| 14 | H | H | 87.6 | not less than 290 |
| 15 | H | $CH_3$ | 95.0 | not less than 290 |
| 16 | 7-$CH(CH_3)_2$ | $CH_3$ | 80.0 | 267–269 (dec.) |
| 17 | H | $(CH_2)_3CH_3$ | 71.4 | 228–230 (dec.) |
| 18 | 7-$CH(CH_3)_2$ | $(CH_2)_3CH_3$ | 87.0 | 220–222 (dec.) |

TABLE 8-continued

| Ex. No. | $R^1$ | $R^4$ | Yield (%) | Melting point (°C.) |
|---|---|---|---|---|
| 19 | 5-$CH(CH_3)_2$ | $(CH_2)_3CH_3$ | 78.8 | 189–191 (dec.) |
| 20 | H | $(CH_2)_5CH_3$ | 87.4 | 202–204 (dec.) |
| 21 | H | $(CH_2)_{17}CH_3$ | 58.6 | 138–140 (dec.) |
| 22 | H | $CH_2CH{=}CH_2$ | 80.1 | 278–280 (dec.) |
| 23 | H | $CH_2CH_2OCH_2CH_3$ | 90.0 | 215–217 |
| 24 | H | $(CH_2)_3CN$ | 75.0 | 276–278 (dec.) |
| 25 | H | $CH_2CH_2CH(C_6H_5)_2$ | 93.1 | 263–265 (dec.) |
| 26 | H | $(CH_2)_2C_6H_5$ | 100.0 | 264–266 (dec.) |
| 27 | 7-$CH(CH_3)_2$ | $(CH_2)_2C_6H_5$ | 100.0 | 265–267 (dec.) |
| 28 | H | $(CH_2)_3C_6H_5$ | 100.0 | 269–271 (dec.) |
| 29 | 7-$CH(CH_3)_2$ | $(CH_2)_3C_6H_5$ | 100.0 | 211–213 (dec.) |
| 30 | 5-$CH(CH_3)_2$ | $(CH_2)_3C_6H_5$ | 100.0 | 223–225 (dec.) |
| 31 | H | $(CH_2)_4C_6H_5$ | 100.0 | 230–232 (dec.) |
| 32 | H | $(CH_2)_5C_6H_5$ | 100.0 | 188–190 (dec.) |
| 33 | H | $CH_2C_6H_4F$(m) | 100.0 | 271–273 (dec.) |
| 34 | H | $CH_2C_6H_4F$(o) | 92.0 | 289–291 (dec.) |
| 35 | H | $CH_2C_6H_4CF_3$(p) | 94.1 | 286–288 (dec.) |
| 36 | H | $CH_2C_6H_4CN$(p) | 94.9 | 251–253 (dec.) |
| 37 | H | $CH_2C_6H_4COOC_2H_5$(p) | 95.0 | 279–281 (dec.) |
| 38 | H | $CH_2C_6H_4COOH$(p) | 90.0 | 175–177 |
| 39 | H | $CH_2C_6H_4OCH_3$(p) | 95.0 | 223–225 (dec.) |
| 40 | H | $CH_2C_6H_4OH$(p) | 80.0 | 230–232 (dec.) |
| 41 | H | $CH_2COC_6H_4Cl$(p) | 83.6 | not less than 290 |
| 42 | H | $CH_2CH{=}CHC_6H_5$ | 90.0 | 272–274 (dec.) |
| 43 | H | $CH_2CH_2OC_6H_5$ | 95.0 | 274–276 (dec.) |
| 44 | H | $CH_2SC_6H_5$ | 95.0 | 241–243 (dec.) |
| 45 | H | 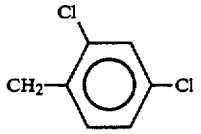 | 71.9 | 285–287 |
| 46 | H | 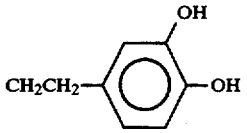 | 71.2 | 288–290 |
| 47 | H | 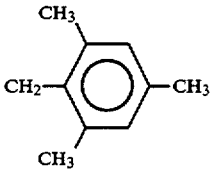 | 82.4 | 279–281 |
| 48 | H | 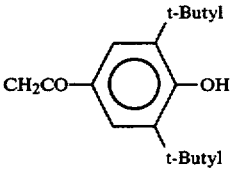 | 99.1 | 288–290 (dec.) |
| 49 | H | 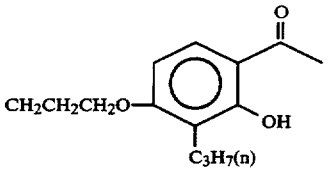 | 100.0 | 222–224 (dec.) |
| 50 | 5-$CH(CH_3)_2$ | 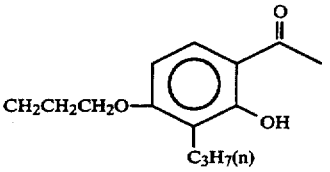 | 95.4 | 110–112 (dec.) |
| 51 | 7-$CH(CH_3)_2$ | $(CH_2)_4C_6H_5$ | 98.9 | 212–214 (dec.) |
| 52 | H | $CH(CH_3)_2$ | 90.0 | 279–281 (dec.) |

TABLE 8-continued

| Ex. No. | $R^1$ | $R^4$ | Yield (%) | Melting point (°C.) |
|---|---|---|---|---|
| 53 | 5-$CH(CH_3)_2$ | 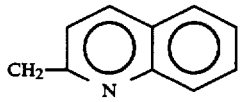 | 94.5 | 290–292 (dec.) |
| 54 | H | $(CH_2)_3Cl$ | 79.3 | 199–201 (dec.) |
| 55 | 5-$CH(CH_3)_2$ | 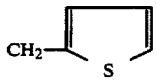 | 98.9 | 236–238 (dec.) |
| 56 | 5-$CH(CH_3)_2$ | $CH_2C_6H_4Cl$(p) | 94.5 | 235–237 (dec.) |
| 57 | 7-$CH(CH_3)_2$ | $CH_2C_6H_4Cl$(p) | 96.8 | 253–255 (dec.) |

TABLE 9

| Ex. No. | MS (m/z) | IR $\nu_{max}^{KBr}$ $cm^{-1}$ |
|---|---|---|
| 14 | 213($M^+$), 170($M^+$—$N_3H$), 157($M^+$—$N_2$—$N_2$) | 3150–2850(CH), 1680–1660(CONH) |
| 15 | 227($M^+$), 184($M^+$—$N_3H$), 171($M^+$—$N_2$—$N_2$) | 3150–2850(CH), 1670–1650(CON) |
| 16 | 269($M^+$), 241($M^+$—$N_2$), 226($M^+$—$N_3H$), 213($M^+$—$N_2$—$N_2$) | 3140–2850(CH), 1680–1660(CON) |
| 17 | 269($M^+$), 226($M^+$—$N_3H$), 213($M^+$—$N_2$—$N_2$), 170($M^+$—$N_3H$—$(CH_2)_4$) | 3150–2850(CH), 1650(CON) |
| 18 | 311($M^+$), 268($M^+$—$N_3H$), 255($M^+$—$N_2$—$N_2$), 240($M^+$—$N_2$—$N_2$—$CH_3$) | 3140–2860(CH), 1680–1670(CON) |
| 19 | 311($M^+$), 255($M^+$—$N_2$—$N_2$), 240($M^+$—$N_2$—$N_2$—$CH_3$) | 3175–2860(CH), 1660–1650(CON) |
| 20 | 297($M^+$), 254($M^+$—$N_3H$), 241($M^+$—$N_2$—$N_2$), 212($M^+$—$N_2$—$N_2$—$C_2H_5$) | 3160–2850(CH), 1660–1640(CON) |
| 21 | 465($M^+$), 437($M^+$—$N_2$), 422($M^+$—$N_3H$), 409($M^+$—$N_2$—$N_2$), 297($M^+$—$(CH_2)_{11}CH_3$) | 3150–2850(CH), 1680–1670(CON) |
| 22 | 253($M^+$), 210($M^+$—$N_3H$), 197($M^+$—$N_2$—$N_2$) | 3140–2860(CH), 1660–1650(CON) |
| 23 | 285($M^+$), 229($M^+$—$N_2$—$N_2$), 213($M^+$—$N_3H$—$C_2H_5$), 197($M^+$—$N_3H$—$OC_2H_5$), 170($M^+$—$NH_3$—$CH_2CH_2OCH_2CH_3$) | 3160–2875(CH), 1680–1670(CON |
| 24 | 280($M^+$), 237($M^+$—$N_3H$), 224($M^+$—$N_2$—$N_2$), 170($M^+$—$(CH_2)_3$ CN—$N_3H$) | 3150–2850(CH), 2230(CN), 1670–1660(CON) |
| 25 | 407($M^+$), 364($M^+$—$N_3H$), 227($M^+$—$CH_2CH(C_6H_5)_2$), 184($M^+$—$N_3H$—$CH_2CH(C_6H_5)_2$) | 3150–2850(CH0, 1670(CON) |
| 26 | 317($M^+$), 274($M^+$—$N_3H$), 261($M^+$—$N_2$—$N_2$) | 3120–2850(CH), 1660–1650(CON) |
| 27 | 359($M^+$), 316($M^+$—$N_3H$), 303($M^+$—$N_2$—$N_2$) | 3160–2850(CH), 1670(CON) |
| 28 | 331($M^+$), 288($M^+$—$N_3H$), 275($M^+$—$N_2$—$N_2$) | 3175–2850(CH), 1650–1640(CON) |
| 29 | 373($M^+$), 345($M^+$—$N_2$), 330($M^+$—$N_3H$), 317($M^+$—$N_2$—$N_2$) | 3140–2850(CH), 1680–1660(CON) |
| 30 | 373($M^+$), 345($M^+$—$N_2$), 330($M^+$—$N_3H$), 317($M^+N_2$—$N_2$), 302($M^+$—$N_2$—$N_2$—$CH_3$) | 3150–2850(CH), 1610–1650(CON) |
| 31 | 345($M^+$), 317($M^+$—$N_2$), 302($M^+$—$N_3H$), 289($M^+$—$N_2$—$N_2$) | 3150–2850(CH), 1660–1640(CON) |
| 32 | 359($M^+$), 331($M^+$—$N_2$), 316($M^+$—$N_3H$), 303($M^+$—$N_2$—$N_2$) | 3160–2850(CH), 1650–1640(CON) |
| 33 | 321($M^+$), 293($M^+$—$N_2$), 278($M^+$—$N_3H$), 265($M^+$—$N_2$—$N_2$) | 3150–2850(CH), 1665–1650(CON) |
| 34 | 321($M^+$), 278($M^+$—$N_3H$), 265($M^+$—$N_2$—$N_2$) | 3160–2850(CH), 1660(CON) |
| 35 | 371($M^+$), 343($M^+$—$N_2$), 328($M^+$—$N_3H$), 315($M^+$—$N_2$—$N_2$) | 3175–2850(CH), 1670(CON) |
| 36 | 328($M^+$), 300($M^+$—$N_2$), 285($M^+$—$N_3H$), 272($M^+$—$N_2$—$N_2$) | 3180–2850(CH), 2220(CN), 1660–1650(CON) |
| 37 | 375($M^+$), 332($M^+$—$N_3H$), 330($M^+$—$OC_2H_5$), 319($M^+$—$N_2$—$N_2$), 302($M^+CO_2C_2H_5$) | 3150–2850(CH), 1715(COO), 1670–1650(CON) |
| 38 | 347($M^+$), 330($M^+$—OH), 304($M^+$—$N_3H$), 302($M^+$—$CO_2H$), 291($M^+$—$N_2$—$N_2$) | 3200–2850(CH), 1710(COO), 1650–1640(CON) |
| 39 | 333($M^+$), 290($M^+$—$N_3H$), 277($M^+$—$N_2$—$N_2$) | 3150–2850(CH), 1660–1650(CON) |
| 40 | 319($M^+$), 276($M^+$—$N_3H$), 263($M^+$—$N_2$—$N_2$) | 3600(OH), 3050–2850(CH), 1680–1670(CON) |
| 41 | 367($M^+$ + 2), 365($M^+$), 322($M^+$—$N_3H$), 297($M^+$—$N_3H$—CN) | 3150–2850(CH), 1685(CO), 1660–1640(CON) |
| 42 | 329($M^+$), 286($M^+$—$N_3H$), 273($M^+$—$N_2$—$N_2$) | 3160–2850(CH), 1670(CON) |
| 43 | 333($M^+$), 290($M^+$—$N_3H$), 277($M^+$—$N_2$—$N_2$) | 3150–2850(CH), 1675(CON) |
| 44 | 335($M^+$), 292($M^+$—$N_3H$), 279($M^+$—$N_2$—$N_2$) | 3130–2850(CH), 1660–1650(CON) |
| 45 | 373($M^+$ + 2), 371($M^+$), 328($M^+$—$N_3H$), 315($M^+$—$N_2$—$N_2$) | 3150–2850(CH), 1660(CON) |
| 46 | 349($M^+$), 306($M^+$—$N_3H$), 281($M^+$—$N_3H$—CN) | 3430(OH), 3150–2850(CH), 1660–1640(CON) |
| 47 | 345($M^+$), 317($M^+$—$N_2$), 302($M^+$—$N_3H$), 289($M^+$—$N_2$—$N_2$), 274($M^+$—$N_2$—$N_2$—$CH_3$) | 3200–2850(CH), 1650(CON) |
| 48 | 459($M^+$), 431($M^+$—$N_2$), 416($M^+$—$N_3H$), 403($M^+$—$N_2$—$N_2$), 388($M^+$—$C_4H_9$—$CH_2$) | 3590(OH), 3140–2850(CH), 1680(CO), 1660(CON) |
| 49 | 447($M^+$), 419($M^+$—$N_2$), 404($M^+$—$N_3H$), 391($M^+$—$N_2$—$N_2$) | 3400(OH), 3200–2850(CH), 1670–1640(CO, CON) |

TABLE 9-continued

| Ex. No. | MS (m/z) | IR $\nu_{max}^{KBr}$ cm$^{-1}$ |
|---|---|---|
| 50 | 489($M^+$), 461($M^+$—$N_2$), 446($M^+$—$N_3H$), 433($M^+$'$N_2$—$N_2$), 416($M^+$—$N_3H$—$CH_3$—$CH_3$) | 3400(OH), 3150–2850(CH), 1660–1640(CO, CON) |
| 51 | 387($M^+$), 359($M^+$—$N_2$), 344($M^+$—$N_3H$), 331($M^+$—$N_2$—$N_2$) | 3130–2850(CH), 1670(CON) |
| 52 | 255($M^+$), 212($M^+$—$N_3H$), 199($M^+$—$N_3$—$CH_2$), 170($M^+$—$N_3H$—$C_3H_7$) | 3200–2850(CH), 1650–1640(CON) |
| 53 | 396($M^+$), 368($M^+$—$N_2$), 353($M^+$—$N_3H$), 340($M^+$—$N_2$—$N_2$), 325($M^+$—$N_2$—$N_2$—$CH_3$) | 3150–2850(CH), 1660(CON) |
| 54 | 301($M^+$ + 2), 289($M^+$), 253($M^+$—HCl), 233(M—$N_2$—$N_2$), 197($M^+$—$N_3H$—$CH_2Cl$) | 3131–2850(CH), 1660–1640(CON) |
| 55 | 351($M^+$), 323($M^+$—$N_2$), 308($M^+$—$N_3H$) 295($M^+$—$N_2$—$N_2$), 280($M^+$—$N_2$—$N_2$—$CH_3$) | 3160–2850(CH), 1660–1650(CON) |
| 56 | 382($M^+$ + 2), 380($M^+$), 337($M^+$—$N_3H$), 324($M^+$—$N_2$—$N_2$) | 3160–2850(CH), 1660–1645(CON) |
| 57 | 382($M^+$ + 2), 380($M^+$), 337($M^+$—$N_3H$), 324($M^+$—$N_2$—$N_2$) | 3160–2850(CH), 1660–1650(CON) |

EXAMPLE 58

[3-Cyano-2-(2,2-diphenylethylamino)-1-azaazulene]

To a solution of 0.38 g (0.002 mol) of 2-chloro-3-cyano-1-azaazulene in 7 ml of dimethylformamide were added 0.43 g (0.0022 mol) of 2,2-diphenylethylamine. The reaction mixture was stirred at room temperature for 24 hours. The reaction mixture was poured into water with ice to allow precipitate to separate out. The precipitate was filtered and dried to give 0.55 g of title compoind (yield: 78.6%).

Melting point: 158°–160° C.

MS m/z: 349 ($M^+$), 246 ($M^+$ —CN —$C_6H_5$), 153 ($M^+$ —$NHCH_2CH(C_6H_5)_2$).

IR (cm$^{-1}$): 3250 (NH), 3050–2800 (CH), 2200 (CN).

EXAMPLE 59

[3-Cyano-2-(3,3-diphenylpropylamino)-1-azaazulene]

The procedures of reaction, treatment and purification of Example 58 were repeated except that 0.46 g (0.0022 mol) of 3,3-diphenylpropylamine was employed instead of 2,2-diphenylethylamine to give title compound (yield: 79%).

Melting point: 178°–180° C.

MS m/z: 363 ($M^+$), 209 ($M^+$ —$C_6H_5$×2), 196 ($M^+$ —$CH(C_6H_5)_2$), 182 ($M^+$ —$CH_2CH(C_6H_5)_2$).

IR (cm$^{-1}$): 3200 (NH), 3100–2800 (CH), 2200 (CN).

EXAMPLE 60

[2-Azido-3-cyano-1-azaazulene]

To a solution of 0.57 g (0.003 mol) of 2-chloro-3cyano-1-azaazulene in 7 ml of dimethylformamide were added 0.3 g (0.0045 mol) of sodium azido. The reaction mixture was stirred at 40° to 50° C. for 30 minutes. The reaction mixture was poured into water with ice, the precipitate was filtered, dried and recrystallized from mixture of chloroform and petroleum ether to give title compound (yield: 94%).

Melting point: 170° C. (dec.).

MS m/z: 195 ($M^+$), 167($M^+$ —$N_2$), 140 ($M^+$ —$N_2$ —$N_2$).

IR (cm$^{-1}$): 3050–2950 (CH), 2200 (CN), 2150–2100 ($N_3$).

EXAMPLE 61

[2-Azido-3-cyano-7-isopropyl-1-azaazulene]

The procedures of reaction, treatment and purification of Example 60 were repeated except that 1.2 g (0.005 mol) of 2-chloro-3-cyano-7-isopropyl-1-azaazulene was employed instead of 2-chloro-3-cyano-1-azaazulene to give title compound (yield: 95.2%).

Melting point: 150°–152° C.

MS m/z: 237 ($M^{30}$), 209 ($M^+$ —$N_2$), 194 ($M^+$ —$N_2$ —$CH_3$).

IR (cm$^{-1}$): 3050–2850 (CH), 2200 (CN), 2150–2140 ($N_3$).

EXAMPLE 62

[3-Cyano-2-carboxymethylamino-1-azaazulene]

To a suspended solution of 3 g (0.016 mol) of 2-chloro-3-cyano-1-azaazulene in 10 ml of dimethylformamide and 50 ml of ethanol were added 6.7 g (0.048 mol) of glycine ethylester hydrochloride and 6.5 g (0.064 mol) of triethylamine. The reaction mixture was heated under reflux for 6 hours. The reaction mixture was concentrated under reduced pressure, the residue was dissolved in chloroform, and the chloroform layer was washed with water and dried. Then, the chloroform was evaporated under reduced pressure to give 3.0 g of 3-cyano-2-ethoxycarbonylmethylamino-1-azaazulene having mp of 186° to 188° C. To a solution of obtained 3-cyano-2-ethoxycarbonylmethylamino-1-azaazulene in 100 ml of ethanol were added 5 to 6 ml of 2N aqueous solution of sodium hydroxide, and the reaction mixture was heated at 60° to 70° C. for 30 minutes. The precipitate of sodium salt of title compound was filtered, washed with ether and dried to give 2.6 g of sodium salt of title compound (yield: 65%).

In 30 ml of water was dissolved 1.0 g of the obtained sodium salt and the solution was neutralized or slightly acidified with dilute hydrochloric acid to precipitate title compound. The title compound could be also obtained by extracting with chloroform several times, drying chloroform layer and distilling away the chloroform under reduced pressure.

Melting point: 260°–262° C. (dec.).

MS m/z: 227 ($M^{30}$), 209 ($M^+$ —$CH_2O$), 181 ($M^+$ —COOH), 169 ($M^+$ —$CH_2COOH$), 154 ($M^+$ —$NHCH_2COOH$).

IR (cm$^{-1}$): 3350 (NH), 3100–2850 (CH), 2200 (CN), 1640–1620 (COO).

EXAMPLE 63

[Sodium salt of 2-carboxymethylamino-3-cyano-5-isopropyl-1-azaazulene]

The procedures of reaction, treatment and purification of Example 62 were repeated except that 0.5 g (0.002 mol) of 2-chloro-3-cyano-5-isopropyl-1-azaazulene was employed instead of 2-chloro-3-cyano-1-azaazulene to give 3-cyano-2-ethoxycarbonylmethylamino-5-isopropyl-1-azaazulene.

Melting point: 152°-154° C.

MS m/z: 297 ($M^{30}$), 224 ($M^+$ —$COOC_2H_5$).

IR ($cm^{-1}$): 3390 (NH), 3050-2850 (CH), 2200 (CN), 1730 (COO).

The compound obtained by the above manner was hydrolyzed in the same manner as in Example 62 to give title compound.

Melting point: 267°-270° C. (dec.).

IR ($cm^{-1}$): 3500-3350 (NH), 3050-2850 (CH), 2200 (CN), 1610, 1410 ($COO^{31}$).

EXAMPLE 64

[3-Cyano-2-(4-(2-methoxyphenyl)piperazinyl)-1-azaazulene]

To a solution of 1.0 g (0.0053 mol) of 2-chloro-3-cyano-1-azaazulene in 20 ml of dimethylformamide were added 0.7 g (0.0053 mol) of anhydrous potassium carbonate and 1.2 g (0.0053 mol) of 2-methoxyphenylpiperadine hydrochloride. The reaction mixture was stirred at room temperature for 24 hours. The reaction mixture was poured into water with ice, and the precipitate was filtered and washed with water. After drying, the precipitate was recrystallized from mixture of ethyl acetate and petroleum ether to give 3.5 g of title compound (yield: 97.2%).

Melting point: 141°-143° C.

MS m/z: 344 ($M^{30}$)

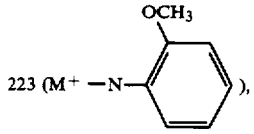

-continued

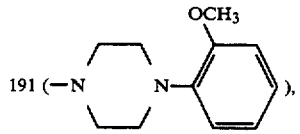

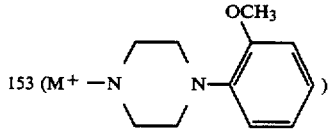

IR ($cm^{-1}$): 3100-2800 (CH), 2200 (CN).

EXAMPLES 65 TO 79

The procedures of reaction, treatment and purification of Example 58 or 62 were repeated except that corresponding starting compounds were employed instead of 2-chloro-3-cyano-1-azaazulene to give compounds represented by the general formula (I'):

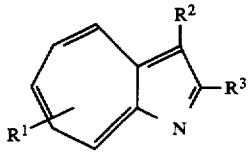

(I')

wherein $R^1$ and $R^3$ were as shown in Table 10, and $R^2$ was cyano group.

Yield and melting point of obtained compounds are shown in Table 10 in which "dec." means decomposition, and MS and IR of obtained compounds are shown in Table 11.

TABLE 10

| Ex. No. | $R^1$ | $R^3$ | Yield (%) | Melting point (°C.) |
|---|---|---|---|---|
| 65 | H | $NHCH(C_6H_5)_2$ | 60.0 | 183-185 |
| 66 | H | $NHC_6H_4COOC_2H_5$(p) | 78.5 | 220-222 |
| 67 | H | $NHC_6H_4COONa$(p) | 80.0 | not less than 280 |
| 68 | H | $NHC_6H_4COOCH_3$(o) | 97.2 | 249-251 |
| 69 | H | 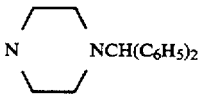 | 90.0 | 228-230 |
| 70 | H | $NHCH(COOC_2H_5)CH_2C_6H_5$ | 67.7 | 82-84 |
| 71 | H | $NHCH(COOH)CH_2C_6H_5$ | 63.2 | 129-131 |
| 72 | H | $NHCH(CH_2OH)COONa$ | 70.0 | 210-213 (dec.) |
| 73 | H | $NHCH(CH_3)COOH$ | 73.0 | 211-213 (dec.) |
| 74 | H | $NH_2.HCl$ | 78.0 | 240-242 (dec.) |
| 75 | H | 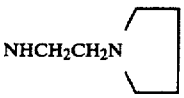 | 67.1 | 133-135 |
| 76 | 5-$CH(CH_3)_2$ | $N_3$ | 86.7 | 145-147 (dec.) |

TABLE 10-continued

| Ex. No. | $R^1$ | $R^3$ | Yield (%) | Melting point (°C.) |
|---|---|---|---|---|
| 77 | H | 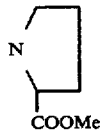 | 80.0 | 120–122 |
| 78 | H | 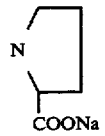 | 95.0 | not less than 280 |
| 79 | 7-$CH(CH_3)_2$ | $NHCH_2COONa$ | 78.8 | not less than 280 |

TABLE 11

| Ex. No. | MS (m/z) | IR $\nu_{max}^{KBr}$ $cm^{-1}$ |
|---|---|---|
| 65 | 335($M^+$) | 3200(NH), 3100, 2850(CH), 2200(CN) |
| 66 | 317($M^+$), 288($M^+$—$C_2H_5$), 272($M^+$—$OC_2H_5$), 244($M^+$—$COOC_2H_5$) | 3300(NH), 3050, 2850(CH), 2200(CN), 1620(COO) |
| 67 | | 3300(NH), 3050, 2850(CH), 2200(CN) |
| 68 | 303($M^+$), 288($M^+$—$CH_3$), 272($M^+$—$OCH_3$), 244($M^+$—$COOCH_3$) | 3300(NH), 3150–2850(CH), 2200(CN), 1710(COO) |
| 69 | 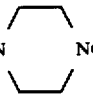 404($M^+$), 251(N NCH($C_6H_5$)$_2$), 237($M^+$—CH($C_6H_5$)$_2$), 222($M^+$—NCH($C_6H_5$)$_2$), 208($M^+$—$CH_2$NCH($C_6H_5$)$_2$) | 3100–2750(CH), 2200(CN) |
| 70 | 345($M^+$), 272($M^+$—$COOC_2H_5$), 254($M^+$—$CH_2C_6H_5$) | 3300(NH), 3050–2850(CH), 2200(CN), 1740(COO) |
| 71 | 317($M^+$), 299($M^+$—$H_2O$), 273($M^+$—$CO_2$), 208($M^+$—$CH_2C_6H_5$—OH) | 3250(NH), 3100–2850(CH), 2200(CN), 1650–1630(COO) |
| 72 | | 3500–3260(OH,NH), 3050–2850(CH), 2200(CN) |
| 73 | 241($M^+$), 223($M^+$—$H_2O$), 197($M^+$—$CO_2$), 168($M^+$—CHCOOH), 154($M^+$—NHCHCOOH) | 3200(NH), 3000–2850(CH), 2200(CN), 1660–1640(COO) |
| 74 | 169($M^+$), 143($M^+$—CN) | 3400($NH_2$), 3300($NH_2$), 2200(CN) |
| 75 | 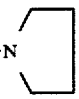 266($M^+$), 196($M^+$—N ), 182($M^+$—$CH_2$N ), 168($M^+$—$CH_2CH_2$N ) | 3750–3250(NH), 2200(CN) |
| 76 | 237($M^+$), 209($M^+$—$N_2$), 194($M^+$—$N_2$—$CH_3$) | 3050–2850(CH), 2200(CN), 2150($N_3$) |
| 77 | 281($M^+$), 250($M^+$—$OCH_3$), 222($M^+$—$COOCH_3$) | 3050–2850(CH), 2200(CN), 1740–1730(COO) |
| 78 | | 3050–2850(CH), 2200(CN), 1600(COO) |
| 79 | | 3500–3350(NH), 3050–2850(CH), 2200(CN), 1610(COO) |

FORMULATION EXAMPLES

The azaazulene derivatives and their pharmaceutically acceptable salts according to the present invention are useful as antiallergic agents and anti-inflammatory agents. Formulations for preparations of a tablet, a capsule, an injection and external preparations such as creams, cataplasmas and inhalations are shown as follows:

(1) According to the following formulation, tablets containing 100 mg of active ingredient per one tablet were prepared.

| components | mg |
|---|---|
| 3-(5-Tetrazolyl)-7-isopropyl-1-(4-fluorobenzyl)-1-azaazulane-2-one | 100 |
| Crystalline cellulose | 50 |
| Calcium carboxymethylcellulose | 10 |
| Sodium lauryl sulfate | 1 |
| Methylcellulose | 3 |
| Calcium stearate | 4 |

(2) According to the following formulation, capsules were prepared by filling each capsule with 200 mg of the mixed components containing 110 mg of active ingredient.

| components | mg |
|---|---|
| 3-(5-Tetrazolyl)-5-isopropyl-1-(4-fluorobenzyl)-1-azaazulane-2-one | 110 |
| Lactose | 45 |
| Corn starch | 35 |
| Crystalline cellulose | 8 |
| Calcium stearate | 2 |

(3) According to the following formulation, injections containing 1.0% active ingredient were prepared.

| components | mg |
|---|---|
| Sodium 3-cyano-5-isopropyl-2-carboxymethylamino-1-azaazulane | 1.0 |
| The Pharmacopoeia of Japan (JP) glucose injection | q.s. |

The formulations are not limited thereto. In addition to the above formulations, other formulations for external preparations, e.g. cream, cataplasmas or inhalant, can be used.

(4) According to the following formulation, cream containing 1.0% active ingredient were prepared.

| components | g |
|---|---|
| 5-isopropyl-3-(5-tetrazolyl)-1-(4-fluorobenzyl)-1-azaazulane-2-one | 10 |
| Myristin isopropyl (made by Nikko Chemicals Ltd.) | 100 |
| Ethanol | 50 |
| Polyoxyethylene monostearate | 10 |
| Carboxyvinyl polymer-940 | 15 |
| Coconuts oil | 30 |

Cream was prepared by diluting the above components with distilled water to be 1000 g in total amount.

What we claim is:

1. An azaazulene derivative having the formula (I):

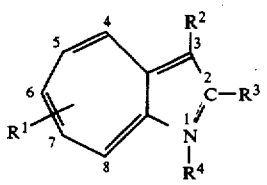

(I)

wherein $R^1$ is hydrogen atom or isopropyl group; the bond C---N between C at the 2-position and N at the 1-position is single bond or double bond; when the bond C---N is single bond, $R^2$ is 5-tetrazolyl group, $R^3$ is taken together with carbon atom to form carbonyl group at the 2-position, and $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring selected from the group consisting of pyridinyl, thienyl and quinolinyl, a diphenyl lower alkyl group, or a lower alkyl group having hydrocarbon-aromatic ring with the formula:

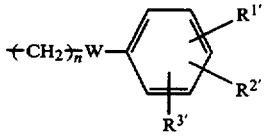

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group; when the bond C---N is double bond, N at the 1-position has no substituent $R^4$, $R^2$ is cyano group, and $R^3$ is [amino group or a salt thereof,] azido group, a diphenyl lower alkyl amino group, a phenyl amino group optionally containing a substituent selected from the group consisting of a lower alkoxy group, a lower alkoxycarbonyl group and a carboxyl group, a piperazinyl group optionally containing a substituent selected from the group consisting of a lower alkoxyphenyl group, a diphenyl lower alkyl group, and a homopiperazinyl group of optionally containing a substituent selected from the group consisting of a lower alkoxyphenyl group and a diphenyl lower alkyl group, an amino acid residue bonded to C-2 at the nitrogen terminus, and lower alkyl esters or salts thereof or a lower alkyl amino group which may have an alkyl amino group or a cycloalkylamino group.

2. The derivative of claim 1, wherein the bond C---N is double bond, $R^2$ is cyano group, $R^3$ is [amino group or a salt thereof;] azido group; a diphenyl lower alkyl amino group; a phenyl amino group substituted by a lower alkoxyl group, carboxyl group or a lower alkoxycarbonyl group; a piperazinyl group substituted by a diphenyl lower alkyl group or a lower alkoxyphenyl group; a homopiperazinyl group substituted by a diphenyl lower alkyl group or a lower alkoxyphenyl group; an amino acid residue bonded by N terminal group in which C terminal group is carboxyl group or a lower alkyl ester thereof; or a lower alkyl amino group which may have an alkyl amino group that may be cyclic one, and $R^1$ is hydrogen atom or isopropyl group.

3. The derivative of claim 1, wherein the bond C---N is single bond, $R^2$ is 5-tetrazolyl group, $R^3$ is taken together with carbon atom at the 2-position to form carbonyl group, $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring, a diphenyl lower alkyl group, or a lower alkyl group having hydrocarbon-aromatic ring with the general formula:

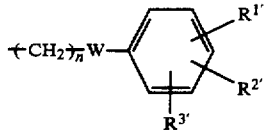

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group, and $R^1$ is hydrogen atom or isopropyl group.

4. The derivative of claim 1 or 2, wherein the derivative is 2-carboxymethylamino-3-cyano-1-azaazulene or a salt thereof.

5. The derivative of claim 1 or 2, wherein the derivative is 2-carboxymethylamino-3-cyano-5-isopropyl-1-azaazulene or a salt thereof.

6. The derivative of claim 1 or 2, wherein the derivative is 2-carboxymethylamino-3-cyano-7-isopropyl-1-azaazulene or a salt thereof.

7. The derivative of claim 1 or 3, wherein the derivative is 3-(5-tetrazolyl)-5-isopropyl-1-(4-fluorobenzyl)-1-azaazulane-2-one or a salt thereof.

8. The derivative of claim 1 or 3, wherein the derivative is 3-(5-tetrazolyl)-1-(4-fluorobenzyl)-1-azaazulane-2-one or a salt thereof.

9. The derivative of claim 1 or 3, wherein the derivative is 3-(5-tetrazolyl)-1-(4-fluorobenzyl)-1-azaazulane-2-one or a salt thereof.

10. The derivative of claim 1 or 3, wherein the derivative is 3-(5-tetrazolyl)-5-isopropyl-1-(4-chlorobenzyl)-1-azaazulane-2-one or a salt thereof.

11. The derivative of claim 1 or 3, wherein the derivative is 3-(5-tetrazolyl)-7-isopropyl-1-(4-chlorobenzyl)-1-azaazulane-2-one or a salt thereof.

12. The derivative of claim 1 or 3, wherein the derivative is 3-(5-tetrazolyl)-1-(4-chlorobenzyl)-1-azaazulane-2-one or a salt thereof.

13. The derivative of claim 1 or 3, wherein the derivative is 3-(5-tetrazolyl)-5-isopropyl-1-(3-phenylpropyl)-1-azaazulane-2-one or a salt thereof.

14. The derivative of claim 1 or 3, wherein the derivative is 3-(5-tetrazolyl)-7-isopropyl-1-(3-phenylpropyl)-1-azaazulane-2-one or a salt thereof.

15. The derivative of claim 1 or 3, wherein the derivative is 3-(5-tetrazolyl)-1-(3-phenylpropyl)-1-azaazulane-2-one or a salt thereof.

16. The derivative of claim 1 or 3, wherein the derivative is 3-(5-tetrazolyl)-5-isopropyl-1-(5-phenylpentyl)-1-azaazulane-2-one or a salt thereof.

17. The derivative of claim 1 or 3, wherein the derivative is 3-(5-tetrazolyl)-7-isopropyl-1-(5-phenylpentyl)-1-azaazulane-2-one or a salt thereof.

18. The derivative of claim 1 or 3, wherein the derivative is 3-(5-tetrazolyl)-1-(5-phenylpentyl)-1-azaazulane-2-one or a salt thereof.

19. The derivative of claim 1 or 3, wherein the derivative is 3-(5-tetrazolyl)-5-isopropyl-1-benzyl-1-azaazulane-2-one or a salt thereof.

20. The derivative of claim 1 or 3, wherein the derivative is 3-(5-tetrazolyl)-7-isopropyl-1-benzyl-1-azaazulane-2-one or a salt thereof.

21. The derivative of claim 1 or 3, wherein the derivative is 3-(5-tetrazolyl)-1-benzyl-1-azaazulane-2-one or a salt thereof.

22. An antiallergic agent containing an effective amount of an azaazulene derivative having the formula (I):

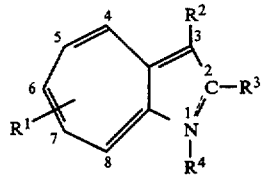

(I)

wherein $R^1$ is hydrogen atom or isopropyl group; the bond C---N between at the 2-position C and N at the 1-position is single bond or double bond; when the bond C---N is single bond, $R^2$ is 5-tetrazolyl group, $R^3$ is taken together with carbon atom to form carbonyl group at the 2-position, and $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring selected from the group consisting of pyridinyl, thienyl and quinolinyl, a diphenyl lower alkyl group, or a lower alkyl group having hydrocarbon-aromatic ring with the formula:

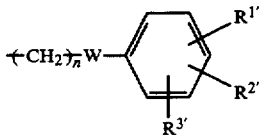

in which W is a single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group; when the bond C---N is double bond, N at the 1-position has no substituent $R^4$, $R^2$ is cyano group, and $R^3$ is [amino group or a salt thereof,] azido group, a diphenyl lower alkyl amino group, a phenyl amino group optionally containing a substituent selected from the group consisting of a lower alkoxy group, lower alkoxycarbonyl group and a carboxyl group, a piperazinyl group optionally containing s substitutent selected from the group consisting of a lower alkoxyphenyl group, a diphenyl lower alkyl group, and a homopiperazinyl group optionally containing a substituent selected from the group consisting of a lower alkoxyphenyl group and a diphenyl lower alkyl group, an amino acid residue bonded to C-2 at the nitrogen terminus, and lower alkyl esters or salts thereof or a lower alkyl amino group which may have an alkyl amino group or a cycloalkylamino group as an active ingredient.

23. An antiinflammatory agent containing an effective amount of an azaazulene derivative having the formula (I):

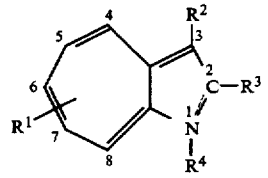

(I)

wherein $R^1$ is hydrogen atom or isopropyl group; the bond C N between C and the 2-position and N at the 1-position is single bond or double bond; when the bond C N is single bond, $R^2$ is 5-tetrazolyl group, $R^3$ is taken together with carbon atom to form carbonyl group at the 2-position, and $R^4$ is hydrogen atom, an alkyl group having 1 to 18 carbon atoms, a lower alkenyl group, a lower alkyl group having oxygen atom or sulfur atom in carbon chain, a lower alkyl group having a halogen atom or cyano group, a lower alkyl group having heteroaromatic ring selected from the group consisting of pyridinyl, thienyl and quinolinyl, a diphenyl lower alkyl group, or a lower alkyl group having hydrocarbon-aromatic ring with the formula:

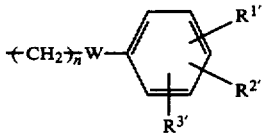

in which W is single bond or carbonyl group, oxygen atom, sulfur atom or —CH=CH—, n is an integer of 1 to 6, and $R^{1'}$, $R^{2'}$ and $R^{3'}$ are the same or different and each is hydrogen atom, a halogen atom, a lower alkyl group, a lower alkoxyl group, trifluoromethyl group, hydroxyl group, a lower alkoxycarbonyl group, carboxyl group, acetyl group or cyano group; when the bond C---N is double bond, N at the 1-position has no substituent $R^4$, $R^2$ is cyano group, and $R^3$ is [amino group or a salt thereof,] azido group, a diphenyl lower alkyl amino group, a phenyl amino group optionally containing a substituent selected from the group consisting of a lower alkoxy group, a lower alkoxycarbonyl group and a carboxyl group, a piperazinyl group optionally containing a substituent selected from the group consisting of a lower alkoxyphenyl group, a diphenyl lower alkyl group, and a homopiperazinyl group optionally containing a substitutent selected from the group consisting of a lower alkoxyphenyl group and a diphenyl lower alkyl group, an amino acid residue bonded to C-2 at the nitrogen terminus, and lower alkyl esters or salts thereof or a lower alkyl amino group which may have an alkyl amino group or a cycloalkylamino group as an active ingredient.

* * * * *